United States Patent
Clark et al.

(10) Patent No.: US 9,873,112 B2
(45) Date of Patent: Jan. 23, 2018

(54) DEHYDRATION-HYDROLYSIS PROCESSES AND CATALYSTS THEREFOR

(71) Applicants: BP CHEMICALS LIMITED, Sunbury-on-Thames, Middlesex (GB); Thomas Edward Clark, Saltend, Hull, East Yorkshire (GB); Evert Jan Ditzel, Saltend, Hull, East Yorkshire (GB); David John Law, Saltend, Hull, East Yorkshire (GB); Bruce Leo Williams, Brough, East Yorkshire (GB)

(72) Inventors: Thomas Edward Clark, East Yorkshire (GB); Evert Jan Ditzel, East Yorkshire (GB); David John Law, East Yorkshire (GB); Bruce Leo Williams, East Yorkshire (GB)

(73) Assignee: BP CHEMICALS LIMITED, Middlesex (GB)

(*) Notice: Subject to any disclaimer, the term of this patent is extended or adjusted under 35 U.S.C. 154(b) by 0 days.

(21) Appl. No.: 14/767,633

(22) PCT Filed: Feb. 13, 2014

(86) PCT No.: PCT/EP2014/052843
§ 371 (c)(1),
(2) Date: Aug. 13, 2015

(87) PCT Pub. No.: WO2014/125038
PCT Pub. Date: Aug. 21, 2014

(65) Prior Publication Data
US 2015/0375217 A1    Dec. 31, 2015

(30) Foreign Application Priority Data
Feb. 15, 2013 (EP) .................................. 13155521
Aug. 16, 2013 (EP) .................................. 13180643

(51) Int. Cl.
*B01J 29/65* (2006.01)
*B01J 37/08* (2006.01)
*C01B 39/44* (2006.01)
*C07C 51/09* (2006.01)
*C07C 41/09* (2006.01)

(52) U.S. Cl.
CPC ............... *B01J 29/65* (2013.01); *B01J 37/08* (2013.01); *C01B 39/445* (2013.01); *C07C 41/09* (2013.01); *C07C 51/09* (2013.01); *C01P 2002/60* (2013.01)

(58) Field of Classification Search
CPC .......... B01J 29/65; B01J 37/08; C07C 51/09; C07C 41/09; C01B 39/445; C01P 2002/60
USPC .......................... 562/607; 423/706; 568/698
See application file for complete search history.

(56) References Cited

U.S. PATENT DOCUMENTS

| 3,992,466 A | 11/1976 | Plank et al. |
| 4,016,245 A | 4/1977 | Plank et al. |
| 5,288,475 A | 2/1994 | Chang et al. |
| 6,521,783 B1 | 2/2003 | Wegman et al. |
| 6,740,783 B1 | 5/2004 | Jun et al. |
| 2009/0326281 A1 | 12/2009 | Appel et al. |

FOREIGN PATENT DOCUMENTS

| EP | 0 012 473 A1 | 6/1980 |
| EP | 0 236 590 A1 | 9/1987 |
| EP | 2 292 578 A1 | 3/2011 |
| KR | 10-2009-0131560 | 12/2009 |
| WO | WO 94/08920 A1 | 4/1994 |
| WO | WO 2011/027105 A1 | 3/2011 |

OTHER PUBLICATIONS

Chauhan et al. Synthesis of zeolite ferrierite—Role of emulsifiers. Indian Journal of Chemical Technology vol. 18, pp. 335-342, September 2DI I.*
Seung-Chan Baek, et al; "Influence of Catalytic Functionalities of Zeolites on Product Selectivities in Methanol Conversion"; *Energy & Fuels*; vol. 23(2); pp. 593-598 (2009).
Nahid Khandan, et al; "Determining an optimum catalyst for liquid-phase dehydration of methanol to dimethyl ether"; *Applied Catalysis A: General*; vol. 349, Issues 1-2, pp. 6-12 (2008).

* cited by examiner

*Primary Examiner* — Yih-Horng Shiao
(74) *Attorney, Agent, or Firm* — Nixon & Vanderhye P.C.

(57) ABSTRACT

Process for the co-production of acetic acid and dimethyl ether by contacting methyl acetate and methanol in the presence of a catalyst containing a crystalline zeolite having a FER framework type. The zeolite has crystallites having a dimension of about 500 nm or less in the c-axis.

13 Claims, 9 Drawing Sheets

DEHYDRATION-HYDROLYSIS PROCESSES AND CATALYSTS THEREFOR

This application is the U.S. national phase of International Application No. PCT/EP2014/052843, filed Feb. 13, 2014 which designated the U.S. and claims priority to European Patent Application Nos. 13155521.1, filed Feb. 15, 2013, and 13180643.2, filed Aug. 16, 2013, the entire contents of each of which are hereby incorporated by reference.

The present invention relates to improved zeolites having a FER framework type, a method of preparing them and their use in dehydration-hydrolysis reactions of alcohols and esters.

BACKGROUND OF THE INVENTION

Zeolites are classified by the Structure Commission of the International Zeolite Association according to the rules of the IUPAC Commission on Zeolite Nomenclature. According to this classification, framework type zeolites for which a structure has been established are assigned a three letter code and are described in the Atlas of Zeolite Framework Types, C. H. Baerlocher, L. B. Mccusker and D. H. Olson, 6th Revised Edition, Elsevier, Amsterdam, 2007 and is also available at C. H. Baerlocher, L. B. Mccusker Database of Zeolite Structures: www.iza-online.org.

One known zeolite for which a structure has been established is the material designated as FER which is a crystalline aluminosilicate which consists of channels of 10-membered rings running parallel to the c-axis interconnected by channels of eight-membered rings running parallel to the b-axis and six-membered channels running parallel to the a-axis.

A number of zeolites having a FER framework type have been synthesised, including ferrierite and ZSM-35, for example U.S. Pat. No. 4,016,245 and U.S. Pat. No. 3,992,466. U.S. Pat. No. 4,016,245 describes a preparation for the zeolite ZSM-35 and its use in catalytic conversion of hydrocarbons. The zeolite has a composition expressed in terms of mole ratios of oxides $(0.3-2.5)R_2O:(0-0.8)M_2O:Al_2O_3:>8$ $SiO_2$ wherein R is an organic nitrogen-containing cation and M is an alkali metal cation and is characterised by a specified X-ray powder diffraction pattern. U.S. Pat. No. 3,992,466 describes a process for converting hydrocarbons in the presence of a catalyst comprising a ZSM-35 crystalline aluminosilicate which serve to retard catalyst aging during the hydrocarbon conversion reaction.

Zeolites having the FER framework type have been found useful to catalyse the dehydration of methanol to dimethyl ether. The use of ferrierite in its hydrogen form to catalyse the dehydration of methanol is described, for example in the publications US 20090326281A, "Influence of catalytic functionalities of zeolites on product selectivities in methanol conversion" Seung-Chan Baek et al. Energy & Fuels, 2009, 23(2), pages 593-598 and "Determining an optimum catalyst for liquid-phase dehydration of methanol to dimethyl ether" Khandan, N et al. Applied Catalysis: General, vol. 349, Issues 1-2, 31 Oct. 2008, pages 6-12.

U.S. Pat. No. 6,740,783 describes an improved process for the preparation of dimethyl ether via the dehydration of a water-containing methanol feed in the presence of a zeolite catalyst in which zeolite the hydrogen cations are partially replaced with metal ions of Groups IA, IIA, IB and IIB of the Periodic Table or ammonium ions.

Korean patent application, KR 2009131560A describes the preparation of dimethyl ether by dehydrating methanol at 200-350° C. and 1-50 atmospheres pressure in the presence of a ferrierite based catalyst or a catalyst obtained by the partial introduction of alkali metal and/or alkaline earth metal ions.

U.S. Pat. No. 6,521,783 describes a process in which acetic acid, methyl acetate, methanol, dimethyl ether and water are fed to a hydrolysis/dehydration reactor which contains an ester hydrolysis catalyst and an alcohol dehydration catalyst which can be the same or different. The alcohol dehydration catalyst can be selected from a solid acid, heteropolyacids, acidic zeolites, titania or silica promoted alumina, aluminium phosphate or tungsten oxide supported on silica-alumina. The ester hydrolysis catalyst can be selected from acidic ion-exchange resins, acidic gamma alumina, fluorinated alumina, sulphate or tungstate promoted zirconia, titania or silica promoted alumina, aluminium phosphate, tungsten oxide supported on silica-alumina, clays, supported mineral acids, zeolites or heteropolyacids. In an example reported in this US patent the nature of the catalyst is not identified.

WO 2011027105 describes the production of acetic acid and dimethyl ether from methanol and methyl acetate at a temperature of 140 to 250° C. in the presence of a zeolite catalyst. The zeolite has a 2-dimensional channel system comprising at least one channel having a 10-membered ring. The zeolites identified as being of this type include ferrierite, ZSM-35 and clinoptilolite.

WO 9408920 describes a process for the highly selective skeletal isomerisation of linear olefin-containing organic feeds wherein linear olefins are contacted with a catalyst comprising ZSM-35, preferably microcrystalline ZSM-35 having its largest crystal dimension no greater than 0.5 microns, under isomerisation conditions to produce isoolefins of corresponding carbon number.

Typically, zeolites, including those having a FER framework type, experience a decline in catalytic activity with the duration of their use which typically results in a loss of productivity to the desired products. This deactivation of the catalyst necessitates costly and time consuming regeneration processes to restore activity to the catalyst. Thus, means for extending the useful life of such zeolite catalysts is an on-going commercial objective. Consequently, it would be highly desirable to retard the aging of catalysts comprising zeolites having a FER framework type during their use in simultaneous dehydration-hydrolysis reactions of alcohols and esters, and in particular during their use in the conversion of methyl acetate and methanol by dehydration-hydrolysis to co-produce acetic acid and dimethyl ether.

SUMMARY OF THE INVENTION

It has now been found that the use of a zeolite having a FER framework type and a crystallite dimension in the c-axis of about 500 nanometers (nm) or less serves to improve the catalytic performance and retard aging of the catalyst during dehydration-hydrolysis reactions such as conversions of methanol and methyl acetate to co-produce acetic acid and dimethyl ether which are carried out in the presence of FER type zeolite catalysts.

Accordingly, the present invention provides a crystalline zeolite having a FER framework type wherein the crystallites have a dimension in the c-axis of about 500 nanometers (nm) or less.

The FER zeolite of the present invention has very small crystals, the crystallites having a dimension in the c-axis of about 500 nm or less. It will be evident to those skilled in the art that, in respect of the crystallites of a zeolite having a FER framework type, the c-axis runs parallel to the channels of the 10-membered rings, the b-axis runs parallel to the channels of the eight-membered rings and the a-axis runs parallel to the six-membered channels. Crystallite dimensions can be determined using conventional techniques such as high resolution scanning electron microscopy (SEM) and transmission electron microscopy (TEM).

The crystallites of the FER type zeolite of the present invention have a dimension in the c-axis of about 500 nm or less, for example of from about 50 nm to about 500 nm. Suitably, the crystallites have a dimension in the c-axis of about 350 nm or less, for example of from about 50 nm to about 350 nm. Preferably, the crystallites have a dimension in the c-axis of from about 250 nm or less, for example from about 50 nm to about 250 nm.

Suitably, the FER type zeolite of the present invention has predominantly crystallites which are less than 350 nm in the c-axis dimension.

In one embodiment, the crystallites of the FER type zeolite have a dimension in the c-axis of about 350 nm or less, for example from about 50 nm to about 350 nm, and at least about 50%, such as at least about 70% of the crystallites have a dimension in the c-axis of about 250 nm or less.

In another embodiment, the crystallites of the FER type zeolite have a dimension in the c-axis of about 500 nm or less, for example from about 50 nm to about 500 nm, and at least about 50%, such as at least about 70% of the crystallites have a dimension in the c-axis of about 250 nm or less, for example of from about 50 nm to about 250 nm.

Suitably, the crystallites are of dimensions such that the ratio of the dimension in the c-axis to the dimension in the b-axis is less than or equal to 3:1, for example less than 3:1 and suitably less than or equal to 2:1, such as less than 2:1. However, other ratios may be employed such as greater than or equal to 4:1, for example greater than or equal to 5:1, such as 5 to 11:1. In some or all embodiments of the present invention, the ratio of the dimension in the c-axis to the dimension in the b-axis is 3:1 to 1:3, such as 3:1 to 1:1.

In an embodiment of the present invention, the crystallites of the FER type zeolite have a dimension in the c-axis of about 500 nm or less, for example of from about 50 nm to about 500 nm, and the ratio of the dimension of the c-axis to the dimension of the b-axis is less than or equal to 3:1, for example less than 3:1, and preferably less than or equal to 2:1, such as less than 2:1.

In an embodiment, the crystallites of the FER type zeolite have a dimension in the c-axis of about 500 nm or less, for example of from about 50 nm to about 500 nm, such as from about 50 to about 250 nm and the ratio of the dimension of the c-axis to the dimension of the b-axis is greater than or equal to 5:1, for example 5 to 11:1.

In another embodiment of the present invention, the crystallites of the FER type zeolite have a dimension in the c-axis, of about 350 nm or less, for example from about 50 nm to about 350 nm, preferably of about 250 nm or less, such as from about 50 nm to about 250 nm, and the ratio of the dimension of the c-axis to the dimension of the b-axis is less than or equal to 3:1, for example less than 3:1, and preferably less than or equal to 2:1, such as less than 2:1.

In a further embodiment, the crystallites of the FER type zeolite have a dimension in the c-axis of about 500 nm or less, for example of about 50 nm to about 500 nm, of which at least about 50%, for example at least about 70% have a dimension in the c-axis of about 250 nm or less, for example of about 50 nm to about 250 nm and the ratio of the dimension of the c-axis to the dimension of the b-axis is less than or equal to 3:1, for example less than 3:1 and preferably less than or equal to 2:1, such as less than 2:1.

In a further embodiment, the crystallites of the FER type zeolite have a dimension in the c-axis of about 350 nm or less, for example of about 50 nm to about 350 nm, of which at least about 50%, such as at least about 70% have a dimension in the c-axis of less than about 250 nm, for example of from about 50 nm to about 250 nm, and the ratio of the dimension of the c-axis to the dimension of the b-axis is less than or equal to 3:1, for example less than 3:1.

In a yet further embodiment of the present invention, at least about 50%, such as at least about 70% of the crystallites of the FER type zeolite have a dimension in the c-axis of about 250 nm or less, for example of about 50 nm to about 250 nm, and the ratio of the dimension of the c-axis to the dimension of the b-axis is less than or equal to 2:1, for example less than 2:1.

In another embodiment at least about 50%, for example at least about 70% of the crystallites of the FER type zeolite have a dimension in the c-axis of about 250 nm or less, for example of about 50 nm to about 250 nm, and the ratio of the dimension of the c-axis to the dimension of the b-axis is equal to or greater than 5:1, for example 5 to 11:1.

In one embodiment, the zeolite of FER framework type of the present invention is selected from ferrierite and ZSM-35, preferably ferrierite.

In another embodiment, the zeolite having a FER framework type of the present invention is in the hydrogen form or substantially in the hydrogen form. In particular, in this embodiment, the zeolite is ferrierite.

In another embodiment of the present invention, the FER type zeolite of the present invention is in alkali metal form. Thus, the FER type zeolite of the present invention, preferably ferrierite, is exchanged or loaded with at least one alkali metal. Suitably, the FER type zeolite of the present invention, preferably ferrierite, has at least 1 mol % of its cation exchange capacity, for example 1 to 60 mol %, such as 1 to 50 mol %, for instance 5 to 50 mol % or 10 to 45 mol % occupied by cations of one or more alkali metals. For the avoidance of doubt by 'alkali metal' is meant the metals of Group I of the Periodic Table and includes Li, Na, K, Rb, Cs and combinations thereof. In particular, the alkali metal is cesium. Thus, suitably, the FER type zeolite of the present invention may be ferrierite in cesium form. In particular, the ferrierite may have 1 to 50 mol %, such as 5 to 50 mol %, for example 10 to 45 mol % of its cation exchange capacity occupied by cesium cations.

The alkali metal content, the silica to alumina mole ratio and the degree of exchange are all related by the expression:

% alkali metal exchange=[moles alkali metal]/
[(moles Al)×100]

These values are determined by any suitable analytical technique (such as elemental analysis, x-ray fluorescence, atomic absorption spectroscopy and inductive coupled plasma analytical techniques) which yields the amount of each element present in a dry alkali metal exchanged zeolite.

BRIEF DESCRIPTION OF THE DRAWINGS

The invention is further described with reference to the accompanying drawings, in which.

DETAILED DESCRIPTION OF THE INVENTION

Figure 1:
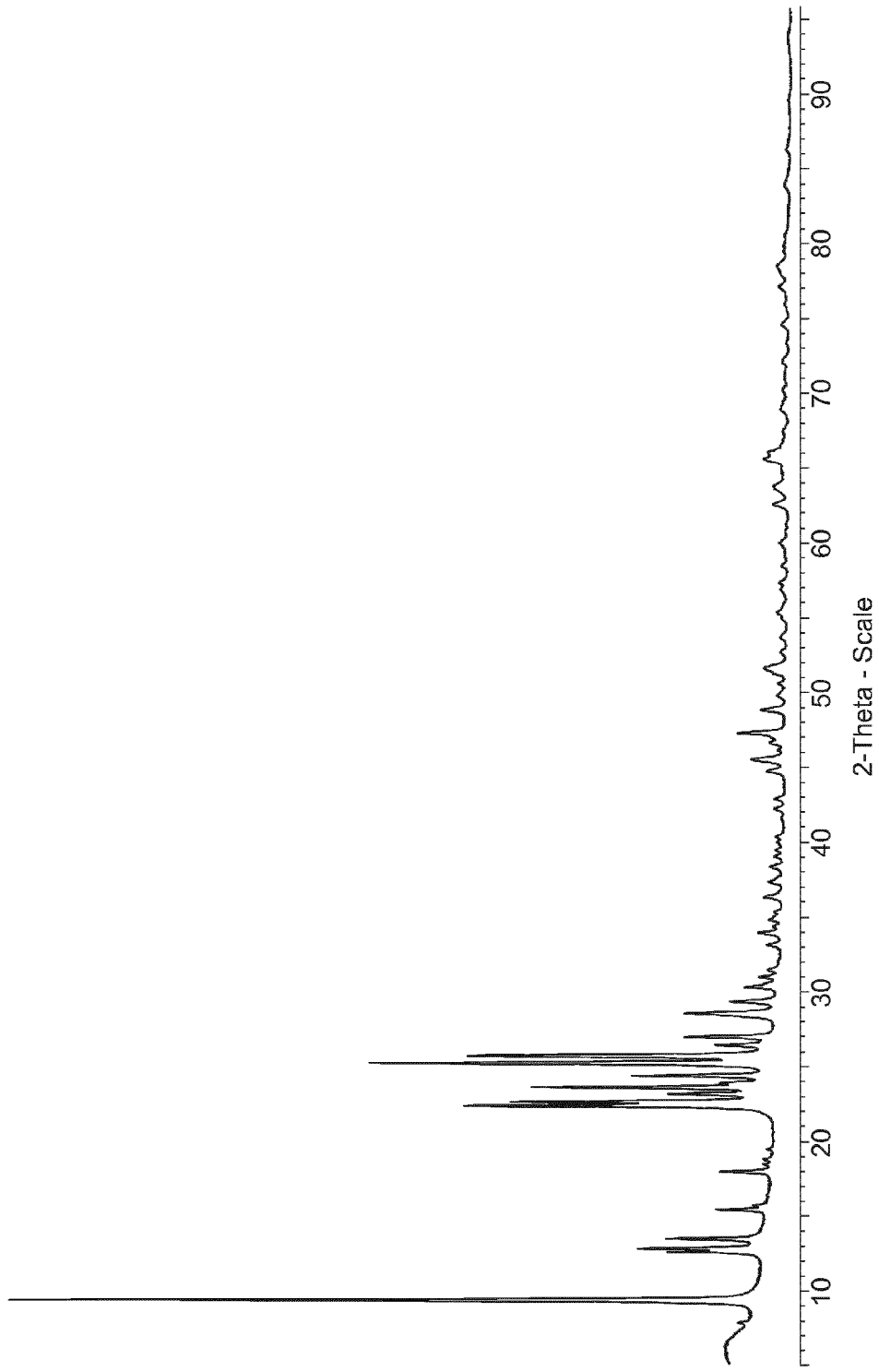
FIG. 1 provides the X-ray diffraction pattern of a small crystallite ferrierite of the present invention.

Zeolites are microporous crystalline structures and transport of molecules through the zeolitic micropores occurs by diffusion and is believed to affect the rate of a reaction. However, the microporous network limits diffusion, hindering access to the active sites and limiting the reaction rate. Attempts have been made to improve catalytic effectiveness by the introduction of mesoporosity into the micropore structure. Mesopores i.e. pores of between 2 and 50 nm provide improved access to the micropores thereby enhancing the rate of diffusion and thus the catalytic performance. Typically, the creation of or increased mesoporosity in a zeolite is introduced by treating a zeolite post-synthesis. Conventional steaming and acid leaching methods or treatment with alkaline media have been applied to alter various properties of zeolites. Treatment with alkaline media removes preferentially silicon from the zeolite framework (desilication) while steaming and acid leaching treatments lead to dealumination. As indicated above, it would be advantageous if the mesoporosity in FER framework type zeolites could be improved as this would result in better accessibility of the zeolite pores and facilitate improved catalytic properties thereof. Advantageously, the FER framework type zeolites of the present invention, as synthesised, have increased mesoporosity compared to conventional as-synthesised large crystal FER framework type zeolites.

Thus, in some or all embodiments of the present invention the FER framework type zeolites (as synthesised) of the present invention have a mesopore volume of at least 0.1 $cm^3/g$, such as 0.1 to 0.2 $cm^3/g$ as measured by $N_2$ absorption.

Zeolites of the present invention can suitably be prepared by forming an aqueous synthesis mixture of silica, alumina, alkali metal and a saturated nitrogen-containing heterocyclic compound and heating said mixture under stirred conditions until the aluminosilicate crystallises. The synthesis mixture, in terms of mole ratios of oxides, suitably has a composition within the following ranges:

|  | Useful | Preferred |
|---|---|---|
| $R^+/(R^+ + M^+)$ | 0.2-1.0 | 0.3-0.9 |
| $OH^-/SiO_2$ | 0.05-0.5 | 0.07-0.49 |
| $H_2O/OH^-$ | 41-500 | 100-250 |
| $SiO_2/Al_2O_3$ | 9-200 | 12-60 | wherein R is a saturated nitrogen-containing heterocyclic compound and M is an alkali metal, usually sodium. The quantity of $OH^-$ is calculated only from the inorganic sources of alkali without any organic base contribution.

Thus, the present invention also provides a method for preparing a crystalline zeolite of the present invention comprising:

a) preparing a synthesis mixture comprising sources of silica, alumina, an alkali metal and a saturated nitrogen-containing heterocyclic compound, said mixture having the following composition, in moles

| $R^+/(R^+ + M^+)$ | 0.2-1.0 |
|---|---|
| $OH^-/SiO_2$ | 0.05-0.5 |
| $H_2O/OH^-$ | 41-500 |
| $SiO_2/Al_2O_3$ | 9-200 | wherein R is a saturated nitrogen-containing heterocyclic compound and M is an alkali metal;

b) heating said mixture at a temperature of 90 to 200° C. with agitation; and c) recovering the FER type zeolite.

Suitably, the synthesis mixture comprises no added sulphuric acid and consists of silica, alumina, alkali metal and a saturated nitrogen-containing heterocyclic compound.

Suitably, the synthesis mixture is basic and has a pH of greater than 7.

The source of silica is typically a colloidal silica, suitably a solution of 20-40 wt % silica in water, such as 30 wt % silica in water, a silica sol or a readily soluble silica gel. The alumina source is typically sodium aluminate or a combination of alumina and sodium hydroxide. In addition to the alkali metal included with the silica and alumina sources, alkali metal hydroxides can be used. Suitably, the alkali metal hydroxide is selected from sodium hydroxide and potassium hydroxide.

A saturated nitrogen-containing heterocyclic compound is employed as an organic structure directing agent in the synthesis mixture. Suitably, the saturated nitrogen-containing heterocyclic compound contains a 5-membered heterocyclic ring or a 6-membered heterocyclic ring in which the heterocyclic ring may contain 1 or more nitrogen atoms, for example 1 to 2 nitrogen atoms. In compounds having 2 or more nitrogen atoms, the nitrogen atoms may be in an ortho, meta or para configuration, suitably a para configuration. The heterocyclic ring may be substituted by one or more alkyl groups, such as by a $C_1$-$C_4$ alkyl group, for example a methyl group and suitably is a N-alkyl saturated nitrogen-containing heterocyclic compound, for example a N-methyl saturated nitrogen-containing heterocyclic compound.

Specific examples of suitable saturated nitrogen-containing heterocyclic compounds having a 5-membered ring and containing 1 nitrogen atom include pyrrolidine and alkyl substituted pyrrolidines, for example N-methyl pyrrolidine. Specific examples of suitable saturated nitrogen-containing heterocyclic compounds having a 6-membered ring and containing 1 nitrogen atom include piperidine. Specific examples of suitable saturated nitrogen-containing heterocyclic compounds having a 6-membered ring and containing 2 nitrogen atoms include piperazine.

In an embodiment, zeolites having a FER framework type and wherein the crystallites have a dimension of about 500 nm or less in the c-axis can suitably be prepared by forming an aqueous synthesis mixture of silica, alumina, alkali metal and a pyrrolidine and heating said mixture under stirred conditions until the aluminosilicate crystallises. The pyrrolidine may an alkyl substituted pyrrolidine. Suitable alkyl substituted pyrrolidines include methyl substituted pyrrolidines, for example N-methyl pyrrolidine, 2-methyl pyrrolidine, 3-methyl pyrrolidine and 2,3-dimethyl pyrrolidine. The synthesis mixture, in terms of mole ratios of oxides, has a composition within the following ranges:

|  | Useful | Preferred |
|---|---|---|
| $R^+/(R^+ + M^+)$ | 0.2-1.0 | 0.3-0.9 |
| $OH^-/SiO_2$ | 0.05-0.5 | 0.07-0.49 |
| $H_2O/OH^-$ | 41-500 | 100-250 |
| $SiO_2/Al_2O_3$ | 9-200 | 12-60 | wherein R is pyrrolidine or an alkyl substituted pyrrolidine, for example a methyl substituted pyrrolidine, such as N-methyl pyrrolidine and M is an alkali metal, usually sodium. The quantity of $OH^-$ is calculated only from the inorganic sources of alkali without any organic base contribution.

In a further embodiment the present invention also provides a method for preparing a crystalline zeolite having a FER framework type wherein the zeolite crystallites have a dimension in the c-axis of about 500 nm or less comprising:
a) preparing a synthesis mixture comprising sources of silica, alumina, an alkali metal and a pyrrolidine, said mixture having the following composition, in moles

| $R^+/(R^+ + M^+)$ | 0.2-1.0 |
|---|---|
| $OH^-/SiO_2$ | 0.05-0.5 |
| $H_2O/OH^-$ | 41-500 |
| $SiO_2/Al_2O_3$ | 9-200 | wherein R is pyrrolidine or an alkyl substituted pyrrolidine, for example a methyl substituted pyrrolidine, such as N-methyl pyrrolidine and M is an alkali metal;
b) heating said mixture at a temperature of 90 to 200° C. with agitation; and
c) recovering the FER type zeolite.

In a further embodiment the present invention also provides a method for preparing a crystalline zeolite having a FER framework type wherein the zeolite crystallites have a dimension of about 500 nm or less comprising:
a) preparing a synthesis mixture comprising sources of silica, alumina, an alkali metal and a piperazine, said mixture having the following composition, in moles

| $R^+/(R^+ + M^+)$ | 0.2-1.0 |
|---|---|
| $OH^-/SiO_2$ | 0.05-0.5 |
| $H_2O/OH^-$ | 41-500 |
| $SiO_2/Al_2O_3$ | 9-200 | wherein R is piperazine or an alkyl substituted piperazine and M is an alkali metal;
b) heating said mixture at a temperature of 90 to 200° C. with agitation; and
c) recovering the FER type zeolite.

The synthesis mixture for preparing the zeolites of the present invention can be prepared by mixing the aqueous reactants until relative homogeneity is obtained. The mixture is then heated with agitation, for example by rotation, tumbling or stirring, and typically under pressure, to a temperature of from about 90° C. to about 200° C., such as about 130° C. to about 180° C., for example from about 130° C. to about 150° C. until crystallisation is complete. Formation of the crystalline product can take anywhere from around 5 hours up to as much as 100 days, such as for 17 days or longer. The duration depends on the temperature employed, with higher temperatures typically requiring shorter crystallisation periods. Suitably, the synthesis mixture is crystallised by heating at a temperature of 130° C. to 150° C. for 17 days or longer. Preferably, the crystallisation is conducted at a temperature in the range of about 130° C. to about 150° C. for up to about 17 days with agitation, for example by rotation, tumbling or stirring.

Upon crystallisation, the crystalline product can be recovered by separating it from the mother liquor, for example by cooling to room temperature, with or without agitation, filtering or centrifuging and water washing. The crystalline product may be dried, for example at temperatures in the range 80° C. to 110° C.

The as-synthesised dried product is ferrierite or ferrierite-type zeolite that does not contain additional crystalline zeolite materials. The FER framework structure is the only crystalline phase present as determined by X-ray diffraction.

Thus, the present invention further provides a crystalline zeolite having a FER framework type having the x-ray diffraction pattern of ferrierite and crystallites having a dimension in the c-axis of about 500 nm or less, suitably of about 350 nm or less, for example of about 250 nm or less.

Preferably, the FER type zeolite as-synthesised has a silica:alumina molar ratio in the range 12 to 60, such as 17 to 55, for example 20 to 55. The bulk silica to alumina molar ratio can be determined by any one of a number of chemical analysis techniques. Such techniques include x-ray fluorescence, atomic absorption and ICP (inductive coupled plasma). All will provide substantially the same silica to alumina molar ratio value.

The crystals of the FER zeolite prepared in accordance hereto exhibit oblong-like or needle-like morphology wherein the dimension in the c-axis is very small, about 500 nm or less, and suitably at least 70% of the crystallites exhibit a c-axis dimension in the range of from about 50 nm to about 350 nm and preferably at least 50% of the crystallites exhibit a c-axis dimension of from about 50 nm to about 250 nm. Where the crystallites have oblong-like morphology they tend to exhibit a ratio of the dimension in the c-axis to the dimension of the b-axis of <3:1, such as <2:1. In contrast, conventionally prepared FER zeolites tend to exhibit platelet-like morphology wherein the dimension in the a-axis is the smallest, on average less than about 0.2 microns (200 nm) and the dimensions of the b-axis and c-axis are much larger, typically an average of greater than about 0.6 microns (600 nm) to about 2 microns (2000 nm).

In some or all embodiments of the present invention the zeolites prepared according to the methods of the present invention comprise an aluminosilicate having an X-ray diffraction pattern substantially as shown in Table 1 below and have a mesopore volume as measured by $N_2$ absorption of at least 0.1 cm$^3$/g, such as 0.1 to 0.2 cm$^3$/g.

The FER type zeolites of the present invention are suitable for use as catalysts in simultaneous dehydration-hydrolysis reactions of alcohols and esters, and, in particular in the conversion of methanol and methyl acetate by dehydration-hydrolysis to acetic acid and dimethyl ether.

Thus, the present invention further provides a process for the co-production of acetic acid and dimethyl ether comprising the step of contacting methyl acetate and methanol in the presence of a catalyst comprising a crystalline zeolite having a FER framework type wherein said zeolite has crystallites having a dimension of about 500 nm or less in the c-axis.

As a result of the crystallisation process, the recovered crystalline zeolite contains within its pores at least a portion of the organic structure directing agent (the saturated nitrogen-containing heterocyclic compound). Thus, the as-synthesised zeolite is treated in a suitable manner to remove the organic structure directing from the zeolite creating zeolite channels open for contact with reactant feedstocks. This is typically accomplished by calcining or essentially heating the zeolite containing the structure directing agent at, for example a temperature of from about 500° C. to about 600° C., suitably under an atmosphere of flowing or static air to yield a calcined FER type zeolite.

A calcined FER type zeolite is preferably converted to the ammonium form by ammonium ion-exchange and is then optionally calcined to yield the FER type zeolite in the hydrogen form or substantially in the hydrogen form. This can be achieved by contacting the calcined FER type zeolite one or more times with a source of ammonium ion to provide the FER zeolite in ammonium-form and calcining the FER zeolite in ammonium form at a temperature of from about 450° C. to about 600° C., such as from about 500° C. to about 600° C., suitably under an atmosphere of flowing or static air.

Thus, the present invention further provides for a method for preparing a hydrogen form of a zeolite of FER framework type which has crystallites having a dimension in the c-axis of from about 500 nm or less which further comprises the steps:

d) removing at least a portion of the saturated nitrogen-containing heterocyclic compound present in a recovered FER type zeolite by heating it at a temperature from about 500° C. to about 600° C. to obtain a calcined zeolite;

e) contacting the calcined zeolite with a source of ammonium ion to provide an ammonium ion-exchanged zeolite; and f) calcining the ammonium ion-exchanged zeolite at a temperature from about 450° C. to about 600° C. to obtain a hydrogen form FER type zeolite.

In another embodiment of the present invention, the catalyst may comprise a small crystallite FER type zeolite of the present invention in an alkali metal form. Thus, suitably the catalyst is a FER zeolite of the present invention, preferably ferrierite, which is exchanged or loaded with at least one alkali metal. Suitably, the FER type zeolite, preferably ferrierite, has at least 1 mol % of its cation exchange capacity, for example 1 to 60 mol %, such as 1 to 50 mol %, for instance 5 to 50 mol % or 10 to 45 mol % occupied by cations of one or more alkali metals. In particular, in this embodiment, the alkali metal is cesium. Thus, suitably, the catalyst may be a ferrierite of the present invention in cesium form. In particular, the ferrierite may have 1 to 50 mol %, such as 5 to 50 mol %, for example 10 to 45 mol % of its cation exchange capacity occupied by cesium cations.

The FER type zeolites of the present invention may be converted into alkali metal form by exchanging at least 1 mol % of the cation exchangeable sites of the FER type zeolite by cations of one or more alkali metals. The conversion of the FER type zeolite of the present invention into an alkali metal form may be carried out using any suitable metal exchange technique. Suitable metal exchange techniques include the well-known techniques of ion-exchange, impregnation and incipient wetness.

Ion-exchange of the FER type zeolite of the present invention by one or more alkali metals may be achieved simply by contacting the hydrogen or ammonium form of the zeolite with a source of alkali metal ions, such as an aqueous solution containing alkali metal cations, for example a solution of alkali metal cations in de-ionised water. After contact of the zeolite with the aqueous solution of the alkali metal(s), the zeolite may be filtered to remove excess metal solution and the zeolite washed with water and then dried to produce a dry zeolite having alkali metal cations occupying at least a portion of its cation exchangeable sites.

Thus, the present invention further provides a method for preparing an alkali metal form of a zeolite of FER framework type which has crystallites having a dimension in the c-axis of from about 500 nm or less comprising the steps:

A) contacting a hydrogen form or an ammonium form FER type zeolite of the present invention with a source of alkali metal ion to provide an alkali metal ion-exchanged zeolite having alkali metal cations occupying at least 1 mol % of its cation exchange capacity;

B) washing and drying the alkali metal ion-exchanged zeolite to obtain a dry alkali metal form of the zeolite.

The washing step may be carried out using any suitable solvent, for example water, suitably de-ionised water.

The ion-exchange, washing and drying steps may be repeated as many times as needed to achieve the desired alkali metal exchange level.

As an alternative to ion-exchange, the hydrogen or ammonium form of the FER type zeolite of the present invention may be prepared by an impregnation exchange technique wherein the zeolite is impregnated with a source of alkali metal ion, such as an aqueous solution containing alkali metal cations, for example a solution of alkali metal cations in de-ionised water, to form a slurry of the zeolite which slurry is subsequently dried to produce a dry zeolite having alkali metal cations occupying at least a portion of its cation exchangeable sites.

Thus, the present invention also provides a method for preparing an alkali metal form of a zeolite of FER framework type which has crystallites having a dimension in the c-axis of from about 500 nm or less comprising the steps:

I) contacting a hydrogen form or an ammonium form FER type zeolite of the present invention with a source of alkali metal ion to provide a slurry of alkali metal exchanged zeolite having alkali metal cations occupying at least 1 mol % of its cation exchange capacity;

II) drying the alkali metal exchanged zeolite to obtain a dry alkali metal form of the zeolite.

Suitably, drying of a zeolite having alkali metal ions exchanged thereupon, whether prepared by ion-exchange or impregnation, may be conducted at temperatures in the range, for example 50° C. to 130° C., such as from 50° C. to 100° C. The drying may be conducted in one or more stages. If desired, drying may be conducted under a vacuum.

Where an ammonium form of the FER type zeolite is used to prepare an alkali metal loaded FER zeolite, the alkali metal loaded ammonium zeolite may be calcined before or after drying to convert some or all of the remaining ammonium ions to hydrogen cations. Suitably, calcining is carried out subsequent to drying of the alkali metal loaded ammonium zeolite. Calcining of the alkali metal loaded ammonium FER zeolite may be conducted at elevated temperature such as a temperature of from about 450° C. to about 600° C., for example from about 500° C. to about 600° C., suitably under an atmosphere of flowing or static air.

Any suitable alkali metal salt may be used for the exchange solution of alkali metal cations. Examples of suitable alkali metal salts include alkali metal acetates, alkali metal nitrates, alkali metal formates and alkali metal chlorides.

The catalysts contain the FER type zeolite described above and optionally a binder.

A refractory oxide may serve as a binder material. Examples of suitable refractory oxides are silicas, aluminas, alumina-silicates, magnesium silicates, magnesium aluminium silicates, titanias, zirconias and clays. A preferred binder is an alumina.

Suitably, the refractory oxide binder may be present in the catalyst in an amount in the range of 10 wt % to 90 wt % (based on total dry weight of FER type zeolite and binder).

The catalysts can be utilised in a variety of forms, for example, in powder form, or in the form of a shaped body, such as a pill or extrudate. Extrudates may be formed by extruding a FER type zeolite of the present invention in the presence of a binder and drying and calcining the resulting extrudate.

Catalysts comprising the small crystallite FER type zeolite of the present invention are useful for catalysing the simultaneous dehydration and hydrolysis of a mixture of methanol and methyl acetate to co-produce acetic acid and dimethyl ether.

Catalysts made with the very small FER framework type zeolite crystals of the present invention age at a significantly slower rate and demonstrate superior catalytic activity for dehydration-hydrolysis reactions, compared to corresponding FER type zeolite catalysts containing appreciably larger crystallite sizes. The as-synthesised zeolite crystals of the present invention also have appreciable mesoporosity which facilitates diffusion of the molecules within the zeolite which generally results in improved catalytic performance.

Thus, the present invention further provides a process for the co-production of acetic acid and dimethyl ether comprising the step of contacting methyl acetate and methanol in the presence of a catalyst comprising a crystalline zeolite having a FER framework type of the present invention.

The dehydration-hydrolysis reaction of methanol and methyl acetate can be represented by equations (1) and (2) respectively:

$$2CH_3OH \rightleftharpoons CH_3OCH_3 + H_2O \quad (1)$$

$$CH_3COOCH_3 + H_2O \rightleftharpoons CH_3COOH + CH_3OH \quad (2)$$

Methanol and methyl acetate may be utilised in the process as a mixed feed. Preferably, however the methanol and methyl acetate are utilised as separate feeds.

The molar ratio of methanol and methyl acetate may be any desired ratio but suitably, the molar ratio of methanol:methyl acetate is in the range 1:0.1 to 1:40, for example 1:1 to 1:30, such as 1:1 to 1:10.

The feed to the process comprises methyl acetate and methanol and may also comprise water. The hydrolysis reaction requires water as a reactant. Water may be obtained from the dehydration reaction which produces water in-situ. Preferably however, water is added to the dehydration-hydrolysis process. Water may be present in one or both of the methanol and methyl acetate feeds to the process or it may be supplied as a separate feed to the process. Suitably, water may be fed to the process in an amount in the range 0.1 to 60 mol %, such as in the range 3 to 40 mol %, for example 5 to 30 mol % based on the total feed to the process.

Suitably, the feed to the process comprises methanol, methyl acetate and water.

The methanol and methyl acetate may be used as pure feeds. However, and depending on their source, one or both of methanol and methyl acetate feeds may contain impurities such acetone. It has been found that acetone is detrimental to catalysts of the ferrierite type in that its presence in dehydration-hydrolysis processes which utilise ferrierite-type catalysts leads to an increase in the deactivation rate of the catalyst thereby reducing its lifetime. Advantageously, the catalysts of the present invention have been found to exhibit improved tolerance to acetone and thus allow improved operation of dehydration-hydrolysis processes in which acetone is present as an impurity in the feed(s).

Acetone may be present in one or both of the methanol and methyl acetate feed(s) to the process in an amount of up to 5 mol % based on the total feed to the process. Suitably, acetone is present in one or both of the methanol and methyl acetate feed(s) in an amount of >0 to 5 mol % such as 0.0005 to 5 mol %, for example 0.5 to 5 mol % based on the total feed to the process.

In an embodiment of the process of the present invention, the catalyst comprises ferrierite, preferably ferrierite in its hydrogen form or substantially hydrogen form and wherein one or both of methanol and methyl acetate feeds to the process contain acetone in an amount of from >0 to 5 mol %, such as in an amount of from 0.005 to 5 mol %, for example 0.5 to 5 mol % based on the total feed to the process.

In another embodiment of the process of the present invention, the catalyst, suitably comprising ferrierite, has from 1 to 60 mol %, such as 10 to 45 mol %, or 20 to 50 mol % of its cation exchangeable sites occupied by one or more alkali metal cations, for example cations of one or both of cesium and sodium and wherein one or both of the methanol and methyl acetate feeds to the process contain acetone in a total amount of from >0 to 5 mol %, such as in an amount of from 0.005 to 5 mol %, for example 0.5 to 5 mol % based on the total feed to the process.

Thus, the process may comprise contacting methyl acetate, methanol and at least one of water and acetone in the presence of a catalyst comprising a FER type zeolite of the present invention, and suitably wherein the zeolite is a ferrierite, preferably a ferrierite in alkali metal form, such as ferrierite in cesium form.

A diluent such as an inert gas, for example nitrogen and helium may also be fed to the process.

The process may be carried out in the reaction zone as a vapour phase or as a liquid phase process, for example as a fixed bed process or a slurry phase process.

Where the process is operated as a vapour phase process, the feedstock(s), prior to entering the reaction zone, may be in the liquid phase. However, prior to contact with the zeolite, the liquid phase components should be volatilised, for example, by use of a vaporiser.

The process is suitably carried out at temperatures of from about 170° C. to about 300° C., for example of from about 190° C. to about 280° C. or from about 180° C. to about 250° C.

The process may be carried out at atmospheric pressure or at pressures greater than atmospheric. Where the process is carried out in the liquid phase, it is preferred to operate the process at a total reaction pressure which is sufficient to maintain the dimethyl ether product in solution. Suitably, therefore, the pressure may be at least 40 barg, such as 40 to 100 barg, suitably 40 to 60 barg. Where the process is carried out in the vapour phase, suitable operating pressures are in the range atmospheric to 30 barg, such as 2 to 20 barg, for example 2 to 15 barg or 10 to 30 barg.

The gas hourly space velocity (GHSV) is suitably in the range 500 to 40,000 $h^{-1}$, such as 1,000 to 25,000 $h^{-1}$, for instance 1,000 to 20,000 $h^{-1}$, for example 1,000 to 15,000 $h^{-1}$ The liquid hourly space velocity (LHSV) is suitably in the range 0.2 to 20, such as in the range 0.5 to 10 for example, 0.5 to 5 $h^{-1}$ or in the range 2 to 8 $h^{-1}$.

The process may be operated as either a continuous or a batch process, preferably as a continuous process.

The product stream of the dehydration-hydrolysis of methanol and methyl acetate comprises acetic acid and dimethyl ether. The product stream may optionally further comprise water, unreacted methanol and unreacted methyl acetate. The acetic acid and dimethyl ether may be recovered from the product stream by conventional purification methods, such as by distillation. Dimethyl ether will generally be recovered as an overhead from a distillation column, and the acetic acid will typically be recovered as a bottoms fraction from the column together with any methyl acetate, methanol and water. The acetic acid can be separated from these components by further distillation. The recovered dimethyl ether may be sold or may be used as a feedstock to carbonylation processes for the production of methyl acetate. The acetic acid may be sold or may be used as a feed in other downstream processes, such as the manufacture of vinyl acetate or ethyl acetate.

The invention is now illustrated with reference to the following non-limiting Examples.

EXAMPLE 1

This example illustrates the preparation of the small crystallite FER framework type zeolites according to the present invention. 0.440 g of a 50% m/v solution of sodium hydroxide in deionised water was added to 56.58 g deionised water and 2.153 g sodium aluminate and mixed well using an overhead stirrer (250-300 rpm). 11.80 g pyrrolidine was added with stirring. 53.58 g Ludox (registered trademark of W.R Grace & Co) AS 30 (30 wt % silica in water) was added and stirred until a gel was formed. The gel was charged to an autoclave which was rotated at 15 rpm and heated at 135° C. for 17 days. The autoclave was allowed to cool over a period 2 hours to room temperature under rotation and the solid product was separated from the liquid by filtration, washed with de-ionised water and dried at 90° C. overnight.

A portion of the as-synthesised product was then calcined at 550° C. for 16 hours to remove the pyrrolidine from the pores of the zeolite. 15.2 g of the calcined product was then converted into the ammonium form of ferrierite by ion-exchange with 150 mL 1M ammonium nitrate. The ammonium exchange was conducted at 80° C. for 1 hour and repeated three times. The ion-exchanged product was separated from the liquid by filtration, washed with deionised water and dried at 90° C. overnight. The ammonium exchanged ferrierite was converted into the hydrogen form of ferrierite by calcining in air at 500° C. for 4 hours.

A portion of the hydrogen form ferrierite was pressed, crushed and sieved into particles of 100-160 microns.

Characterisation

The X-ray diffraction pattern of an as-synthesised product was recorded on a Bruker D8 X-ray diffractometer using Cu-K$_\alpha$ radiation that operated at 40 kV and 40 mA.

Scanning electron microscopy (SEM) images were recorded using a LEO 435 VP scanning electron microscope operated at 20 kv set for high vacuum. The sample is pre-coated with Au in a sputter coater for 45 seconds.

The mesopore volume ($V_{mesopore}$(cm$^3$/g)) of a zeolite was determined by N$_2$ adsorption carried out at 77K in a Micromeritics Tristar 3000 apparatus equipped with Tristar 3000 v6.01 software for data analysis. Prior to analysis, a zeolite sample was degassed under vacuum of 5×10$^{-3}$ Torr at 60° C. for 30 minutes and then at 120° C. for 16 hours. The resulting data were reduced using the BET method over the pressure range of p/p$_0$=0.01-0.05 based on a published model [S. Brunauer, P. H. Emmett, E. Teller, J. Am. Chem. Soc. 60 (1938) 309] and the Barrett, Joyner and Halenda method for pore diameters of 2 nm to 100 nm, to yield the surface area and pore size distribution respectively. The t-plot method was used to determine the micropore volume and external surface area using a fitted thickness range of 0.35-0.5 nm [B. C. Lippens, J. H. de Boer, J. Catal. 4 (1965) 319]. The mesopore volume was calculated by substracting the micropore volume from the total pore volume (determined using the single point adsorption total pore volume; p/p$_0$>0.98).

The X-ray diffraction pattern of the as-synthesised product of Example 1 is shown in FIG. 1 and summarised in Table 1 below. The XRD data demonstrated that the product was ferrierite. The ferrierite had a silica:alumina molar ratio of 22.

TABLE 1

X-Ray Diffraction Pattern of As-Synthesised Product of Example 1

| 2 Theta | d(Å) | I/I$_0$ |
| --- | --- | --- |
| 7.77 | 11.37 | 1.5 |
| 9.33 | 9.48 | 100.0 |
| 12.50 | 7.08 | 12.8 |
| 12.73 | 6.95 | 16.9 |
| 13.39 | 6.61 | 13.2 |
| 15.35 | 5.77 | 6.9 |
| 15.63 | 5.67 | 2.1 |
| 17.90 | 4.95 | 7.0 |
| 18.39 | 4.82 | 1.2 |
| 18.73 | 4.74 | 1.5 |
| 19.37 | 4.58 | 1.0 |
| 22.31 | 3.98 | 41.5 |
| 22.58 | 3.94 | 35.2 |
| 23.09 | 3.85 | 14.1 |
| 23.54 | 3.78 | 32.5 |
| 23.82 | 3.73 | 7.3 |
| 24.29 | 3.66 | 19.0 |
| 25.17 | 3.54 | 54.0 |
| 25.65 | 3.47 | 41.0 |
| 26.36 | 3.38 | 7.9 |
| 26.90 | 3.31 | 12.2 |
| 28.48 | 3.13 | 12.2 |
| 29.27 | 3.05 | 6.2 |
| 30.25 | 2.95 | 4.3 |
| 30.91 | 2.89 | 2.7 |
| 31.38 | 2.85 | 1.5 |
| 33.07 | 2.71 | 1.9 |
| 33.89 | 2.64 | 3.0 |
| 34.29 | 2.61 | 1.2 |
| 34.75 | 2.58 | 1.7 |
| 35.26 | 2.54 | 1.0 |
| 36.26 | 2.48 | 2.5 |
| 37.29 | 2.41 | 2.0 |
| 38.31 | 2.35 | 1.6 |
| 39.00 | 2.31 | 1.2 |
| 39.43 | 2.28 | 1.0 |
| 40.31 | 2.24 | 1.0 |
| 42.16 | 2.14 | 1.4 |
| 42.85 | 2.11 | 1.3 |
| 44.70 | 2.03 | 2.4 |
| 45.47 | 1.99 | 4.4 |
| 46.58 | 1.95 | 1.9 |

TABLE 1-continued

X-Ray Diffraction Pattern of As-Synthesised Product of Example 1

| 2 Theta | d(Å) | I/I$_0$ |
|---|---|---|
| 47.23 | 1.92 | 6.2 |
| 48.79 | 1.86 | 3.2 |
| 49.78 | 1.83 | 1.1 |
| 50.58 | 1.80 | 0.9 |

Figure 2:
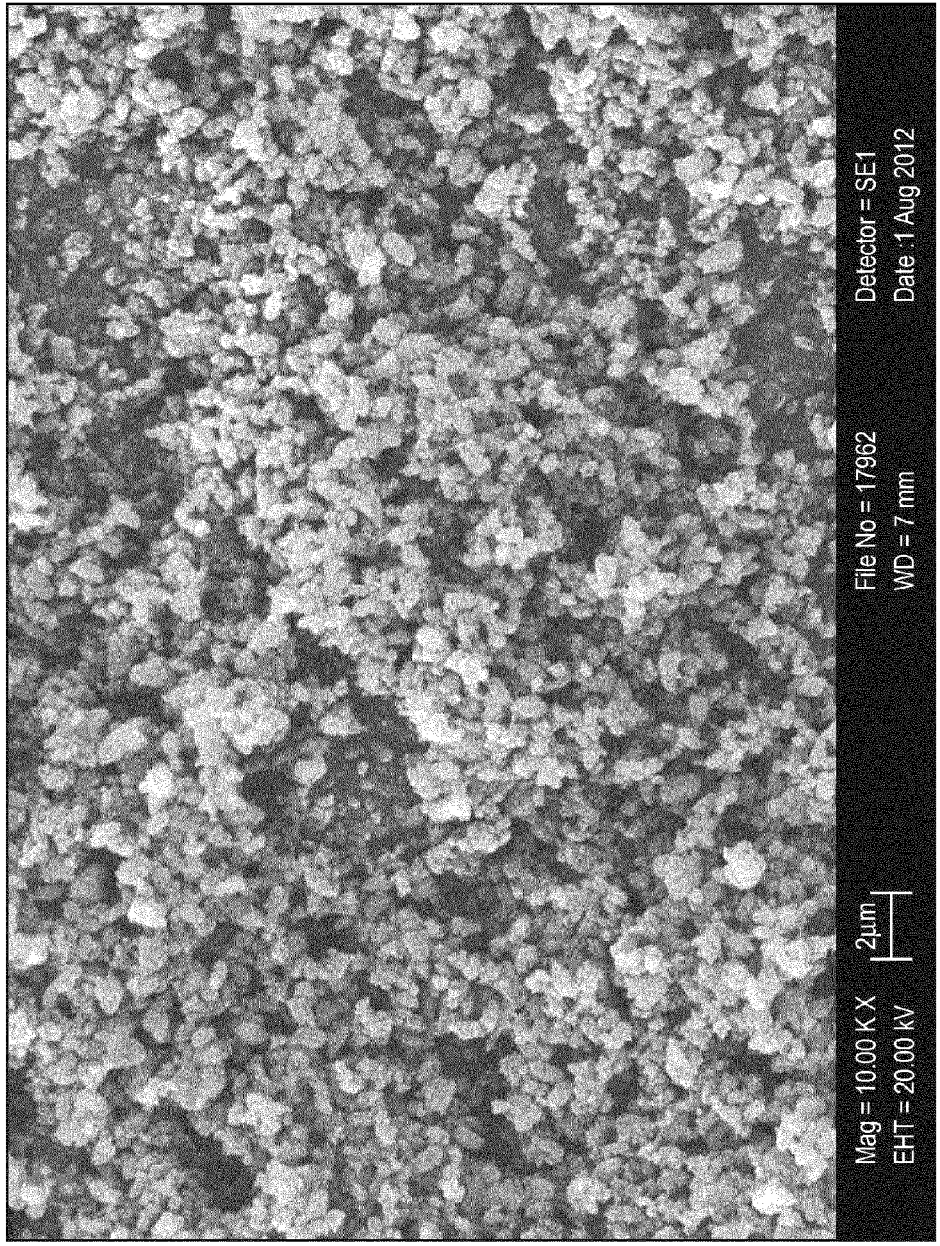
FIG. 2 is a SEM micrograph of a small crystallite ferrierite of the present invention.

The microcrystalline ferrierite prepared in this example was analysed by Scanning Electron Microscopy (SEM). FIG. 2 is a SEM micrograph of the ferrierite produced by the method of Example 1, taken at 10,000× magnification. The ferrierite crystals of the present invention exhibited a well-defined oblong morphology and had a dimension in the c-axis of about 50 to about 350 nm. At least 70% of the crystallites had a c-axis dimension in the range 50 to 250 nm and the ratio of the dimension of the c-axis to the dimension of the b-axis was <3:1.

EXAMPLE A

Figure 3:
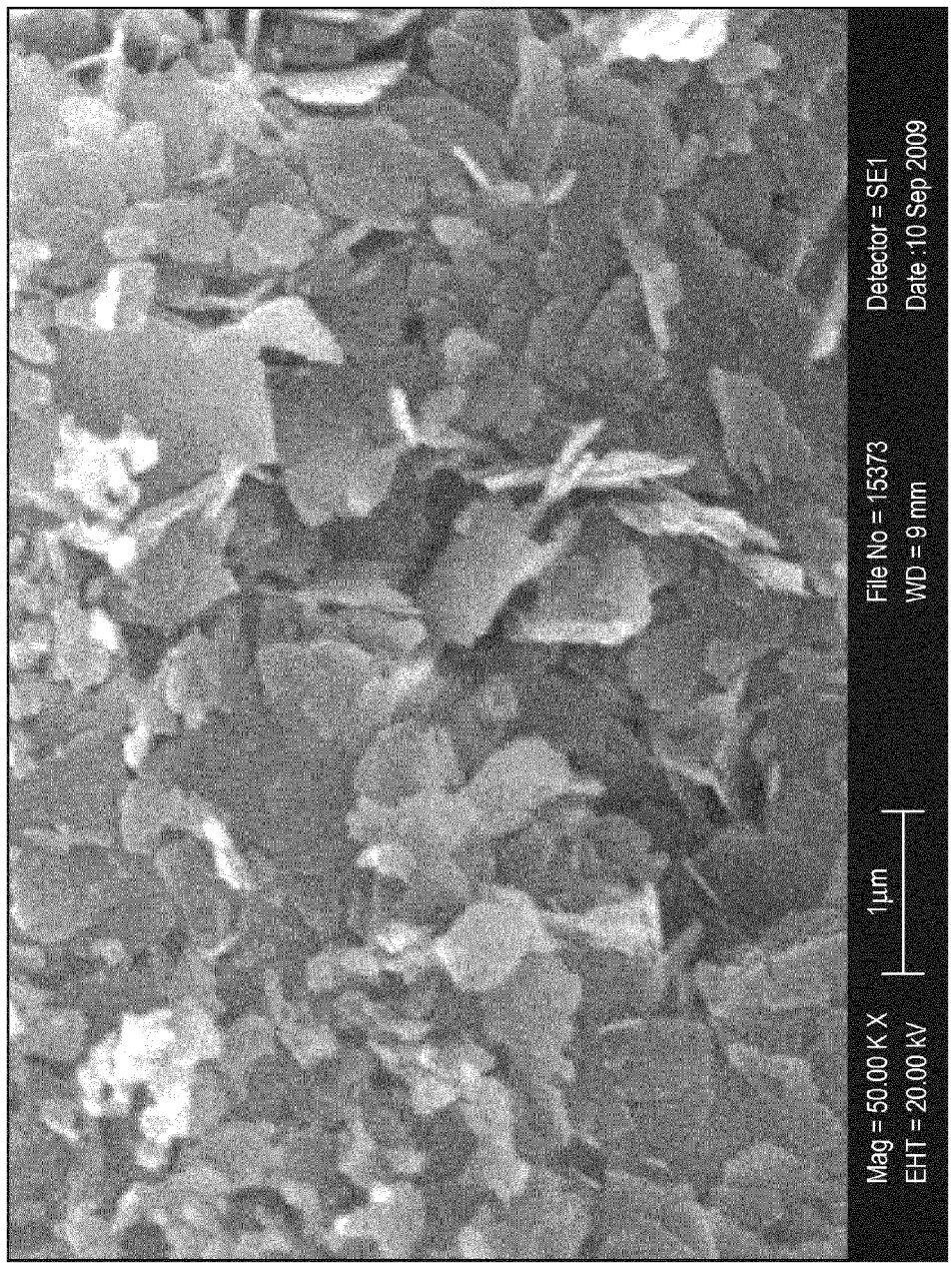
FIG. 3 is a SEM micrograph of a commercially available ferrierite.
Figure 4:
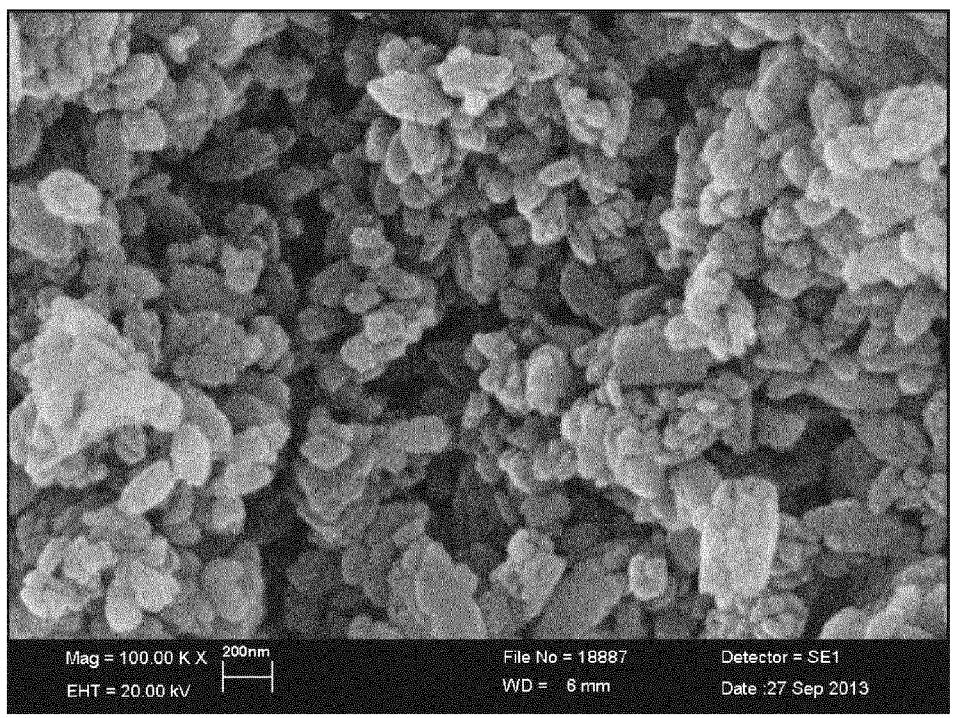
FIG. 4 is a SEM micrograph of a small crystallite ferrierite of the present invention prepared using pyrrolidine structure directing agent.
Figure 5:
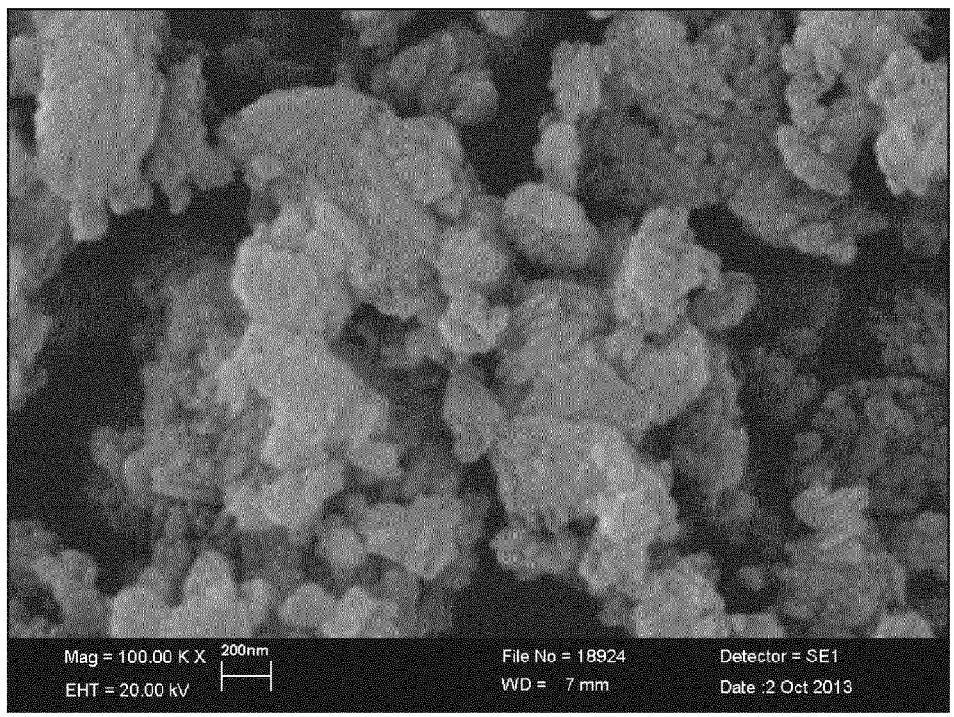
FIG. 5 is a SEM micrograph of a small crystallite ferrierite of the present invention prepared using N-methyl pyrrolidine structure directing agent.
Figure 6:
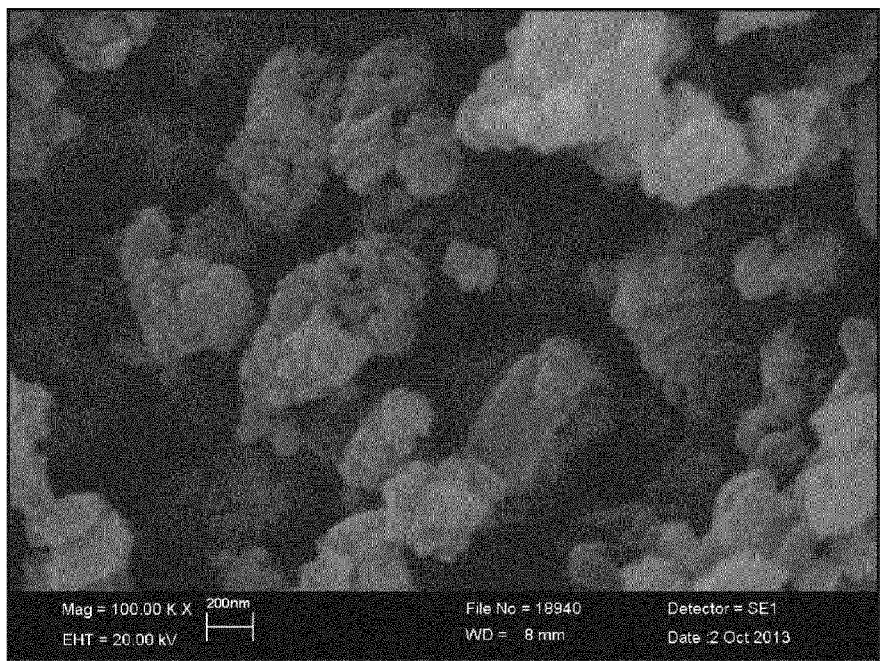
FIG. 6 is a SEM micrograph of a small crystallite ferrierite of the present invention prepared using piperidine structure directing agent.
Figure 7:
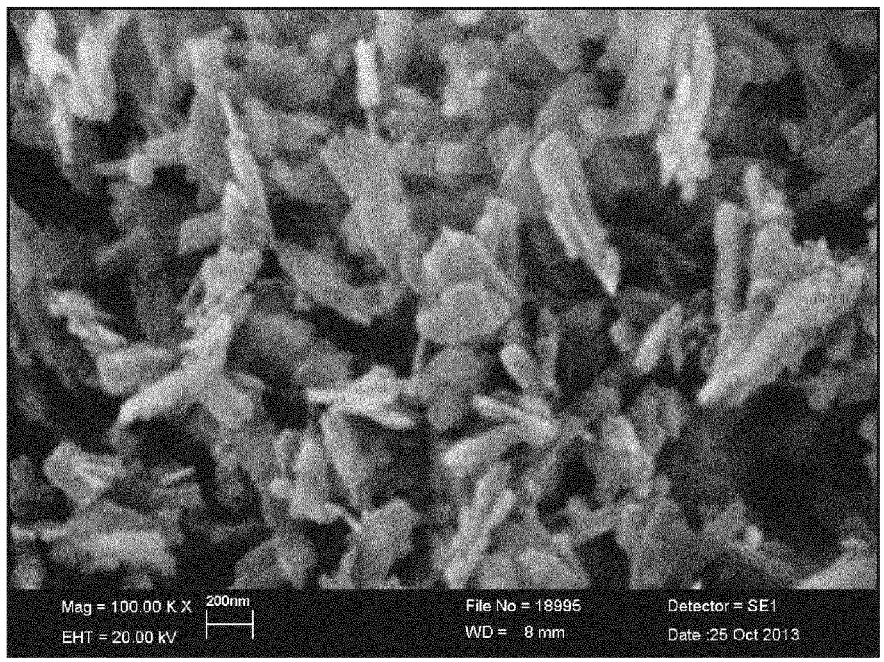
FIG. 7 is a SEM micrograph of a small crystallite ferrierite of the present invention prepared using piperazine structure directing agent.

The catalyst of this Example was a commercially available ferrierite (Tosoh HSZ-720NHA, SAR 17.6) wherein greater than 90% of its crystals had a dimension in the c-axis of greater than 250 nm, the ratio of the dimension of the c-axis to that of the b-axis was greater than 5:1 and the crystals exhibited a platelet-like morphology. FIG. 3 is a SEM micrograph of this ferrierite taken at 50,000× magnification. The catalyst was used in the form of particles sieved to 100-160 microns.

EXAMPLE 2—DEHYDRATION-HYDROLYSIS REACTION

This example illustrates the dehydration-hydrolysis of methanol and methyl acetate conducted in the presence of the catalyst prepared in accordance with Example 1 above and in the presence of the catalyst of Example A.

The dehydration-hydrolysis reactions were carried out in a pressure flow reactor unit consisting of 16 identical parallel isothermal co-current tubular reactors of the type described in, for example WO2006107187. The reactors were arranged in 4 blocks of 4 reactors with each block having an independent temperature control. A reactor tube was loaded with 20 microliters of catalyst particles. The catalyst particles were loaded onto a metal sinter having a pore size of 20 microns and the remainder of the reactor tube was filled with 150 microliters of carborundum. The exit stream from each reactor was periodically analysed by gas chromatography using an Interscience Trace gas chromatograph equipped with two TCD detectors and one FID detector.

Nitrogen and helium at a total gas hourly space velocity of 16,000 h$^{-1}$ were introduced into the reactor. The reactor was pressurised to a pressure of 10 barg and the temperature adjusted to 180° C. A vapour feed of 50 mol % methyl acetate, 30 mol % methanol and 20 mol % water was introduced into the reactor at a gas hourly space velocity of 4,000 h$^{-1}$ for 48 hours. The reactor temperature was then increased from 180° C. to 220° C. for 111 hours before being reduced to 180° C. for a period of 35 hours.

Table 2 below provides the deactivation rates of the catalysts tested in Example 2 for the reaction period conducted at 220° C. The deactivation rates were calculated as % loss in space time yield (STY) of each of the products, dimethyl ether and acetic acid, per day.

TABLE 2

| Catalyst | % STY loss/day Dimethyl Ether | % STY loss/day Acetic Acid |
|---|---|---|
| Ex. A | 1.4 | 3.7 |
| Ex. 1 | 1.0 | 2.2 |

As can be seen from Table 2, the very small crystallite catalyst of the present invention (Ex. 1) demonstrated a significantly lower deactivation rate than the catalyst of larger crystal size (Ex. A)

EXAMPLE 3—DEHYDRATION-HYDROLYSIS REACTION

Dehydration-hydrolysis reactions of methyl acetate and methanol in the presence of the catalysts of Example 1 and Example A were carried out in the apparatus as described in Example 2 above.

Nitrogen and helium at a total gas hourly space velocity of 16,000 h$^{-1}$ were introduced into the reactor. The pressure was increased to 10 barg and the reactor temperature adjusted to 180° C. A vapour feed of 47.5 mol % methyl acetate, 28.5 mol % methanol, 19 mol % water and 5 mol % acetone was introduced at a gas hourly space velocity of 4,000 h$^{-1}$ into the reactor, for 35 hours. The reactor temperature was then increased from 180° C. to 200° C. for 71 hours and then further increased to 220° C. for 71 hours before reducing the temperature to 180° C. for a period of 30 hours.

Table 3 below provides the deactivation rates of the catalysts tested in Example 3 for the reaction period conducted at 200° C.-220° C. The deactivation rates were calculated as % loss in space time yield (STY) of each of the products, dimethyl ether and acetic acid, per day.

TABLE 3

| Catalyst | % STY loss/day Dimethyl Ether | % STY loss/day Acetic Acid |
|---|---|---|
| Ex. A | 11.8 | 11.8 |
| Ex. 1 | 2.8 | 6.4 |

Table 3 clearly illustrates that the very small crystallite catalysts of the present invention (Ex. 1) outperform the larger crystallite catalyst of Example A in the dehydration-hydrolysis reaction. The catalyst of the present invention demonstrates superior resistance to deactivation in the reaction compared to the catalyst of Example A.

EXAMPLE 4—DEHYDRATION-HYDROLYSIS REACTION

The dehydration-hydrolysis of methyl acetate and methanol in the presence of the catalysts of Example 1 and Example A was carried out in the apparatus as described in Example 2 above.

Nitrogen and helium at a total gas hourly space velocity of 16,000 h$^{-1}$ were introduced into the reactor. The reactor was pressurised to 10 barg and the reactor temperature adjusted to 180° C. A vapour feed of 72 mol % methyl acetate, 7.5 mol % methanol, 20 mol % water and 0.5 mol % acetone was introduced at a gas hourly space velocity of 4,000 h$^{-1}$ into the reactor for 140 hours. The reactor temperature was then increased from 180° C. to 210° C. for 110 hours before being reduced to 180° C. for a period of 60 hours after which time the temperature was increased to 230° C. for a period of 115 hours and then reduced to 180° C. for 50 hours. The temperature was then increased from 180° C. to 250° C. and held at this temperature for 100 hours before being reduced to 180° C. for a period of 25 hours.

Table 4 below provides the deactivation rates of the catalysts tested in Example 4 for the reaction periods conducted at 210° C., 230° C. and 250° C. The deactivation rates were calculated as % loss in space time yield (STY) of each of the products, dimethyl ether and acetic acid, per day.

TABLE 4

| Catalyst | Temp. (° C.) | % STY loss/day Dimethyl Ether | % STY loss/day Acetic Acid |
|---|---|---|---|
| Ex. A | 210 | 3.6 | 3.0 |
| Ex. 1 | 210 | 0.6 | 0.6 |
| Ex. A | 230 | 9.2 | 6.2 |
| Ex. 1 | 230 | 1.5 | 1.6 |
| Ex. A | 250 | 14.7 | 7.3 |
| Ex. 1 | 250 | 5.2 | 4.3 |

As can be seen from Table 4, the microcrystalline catalysts of the present invention (Example 1) exhibited superior resistance to deactivation in the dehydration-hydrolysis reaction compared to the larger crystalline material of the catalyst in Example A.

EXAMPLE B—PREPARATION OF ALKALI METAL LOADED FERRIERITES

A series of ferrierite catalysts containing 9.2 mol %, 18.5 mol % and 37.0 mol % Cs were prepared from a commercially available ammonium ferrierite which exhibited (i) crystals of >500 to 2000 nm in the c-axis (as determined by SEM) and (ii) a ratio of the dimension of the c-axis to the b-axis of greater than 3:1.

20 g of the commercially available NH$_4$-ferrierite (SAR of 20), an amount of cesium nitrate (Sigma Aldrich, 99% purity) and 48 ml of de-ionised water were stirred together for 16 hours at ambient temperature to form a slurry. The slurry was dried at a temperature of 80° C. under vacuum at a pressure of 250 mbar and then further dried for 20 hours at 110° C. to produce a dry solid. The solid was calcined for 3 hours at 500° C. under an atmosphere of static air to yield cesium loaded H-ferrierite having a percentage of the cation sites in the ferrierite occupied by cesium as given in Table 5 below.

TABLE 5

| Catalyst | Amount of Cs salt/(g) | Mol % of cation sites occupied by Cs |
|---|---|---|
| A | 0.49 | 9.2 |
| B | 0.98 | 18.5 |
| C | 1.97 | 37.0 |

EXAMPLE 5—PREPARATION OF ALKALI METAL LOADED FERRIERITES

The procedure of Example 1 was repeated to form an ammonium exchanged ferrierite. The ammonium ferrierite so-formed exhibited the X-ray diffraction pattern of ferrierite and its crystallites (as determined by SEM) exhibited a dimension in the c-axis of about 50 to about 350 nm. At least 70% of the crystallites had a c-axis dimension in the range 50 to 250 nm and a ratio of the dimension of the c-axis to the b-axis of less than 3:1.

A series of ferrierite catalysts containing 10.6 mol %, 21.2 mol % and 42.5 mol % cesium were prepared from the ammonium ferrierite in accordance with the following procedure. 4 g of the NH$_4$-ferrierite, an amount of cesium formate (Sigma Aldrich, 98% purity) and 10 ml of de-ionised water were stirred together for 16 hours at ambient temperature to form a slurry. The slurry was dried at a temperature of 80° C. under vacuum at a pressure of 250 mbar and then further dried for 20 hours at 110° C. to produce a dry solid. The solid was calcined for 4 hours at 500° C. under an atmosphere of static air to yield cesium loaded H-ferrierite having a percentage of the cation sites in the ferrierite occupied by cesium as given in Table 6 below.

TABLE 6

| Catalyst | Amount of Cs salt/(g) | Mol % of cation sites occupied by Cs |
|---|---|---|
| D | 0.098 | 10.6 |
| E | 0.195 | 21.2 |
| F | 0.389 | 42.5 |

EXAMPLE 6—DEHYDRATION-HYDROLYSIS REACTIONS

Dehydration-hydrolysis reactions using catalysts A-F as prepared in Examples B and 5 above were carried out in a pressure flow reactor unit consisting of 16 identical parallel isothermal co-current tubular reactors of the type described in, for example WO2006107187. The reactors were arranged in 4 blocks of 4 reactors with each block having an independent temperature control. 0.015 g of a catalyst (in the form of particles of 100-160 microns) was loaded onto a metal sinter (pore size of 20 microns) within a reactor and covered with 150 microliters of carborundum. The exit stream from each reactor was periodically analysed by gas chromatography using an Interscience Trace gas chromatograph equipped with two TCD detectors and one FID detector.

In respect of each reactor, nitrogen and helium gases were introduced therein at a total gas hourly space velocity of 16,000 h$^{-1}$ to provide a pressure of 30 barg. The temperature of the reactor was adjusted to 180° C. A vapour feed (at a gas hourly space velocity of 4,000 h$^{-1}$) comprising 72 mol % methyl acetate, 7.5 mol % methanol, 0.5 mol % acetone and 20 mol % water was introduced into the reactor and brought into contact with the catalyst for 120 hours at a reactor temperature of 180° C. The reaction was then continued for a further 113 hours at an increased temperature of 250° C. and then continued for a further 45 hours at a reduced temperature of 180° C.

Table 7 below provides the deactivation rates for each of the catalysts A-F for the reaction period conducted at 250° C. The deactivation rates were calculated as % loss in space time yield (STY) of each of the products, dimethyl ether and acetic acid, per day.

TABLE 7

| | % STY Loss per Day | |
| --- | --- | --- |
| Catalyst | AcOH | DME |
| A | 9.8 | 10.2 |
| D (Invention) | 0.7 | 0.5 |
| B | 7.7 | 8.3 |
| E (Invention) | 0 | 0.2 |
| C | 2.0 | 3.2 |
| F (Invention) | 0 | 0 |

It can clearly be seen from Table 7 that in respect of catalysts A and D, which nominally have the same cesium loading, that catalyst D, comprising the small ferrierite crystallites of the present invention, exhibits substantially improved deactivation rates compared to catalyst A which has larger ferrierite crystals. Catalysts of the present invention also demonstrate reduced deactivation rates (compared to catalysts not of the invention) at increased levels of cesium. As can be seen from Table 7, catalysts E and F (ferrierites of the present invention) provided far superior deactivation rates compared to the larger crystal catalysts B and C respectively.

Figure 9:
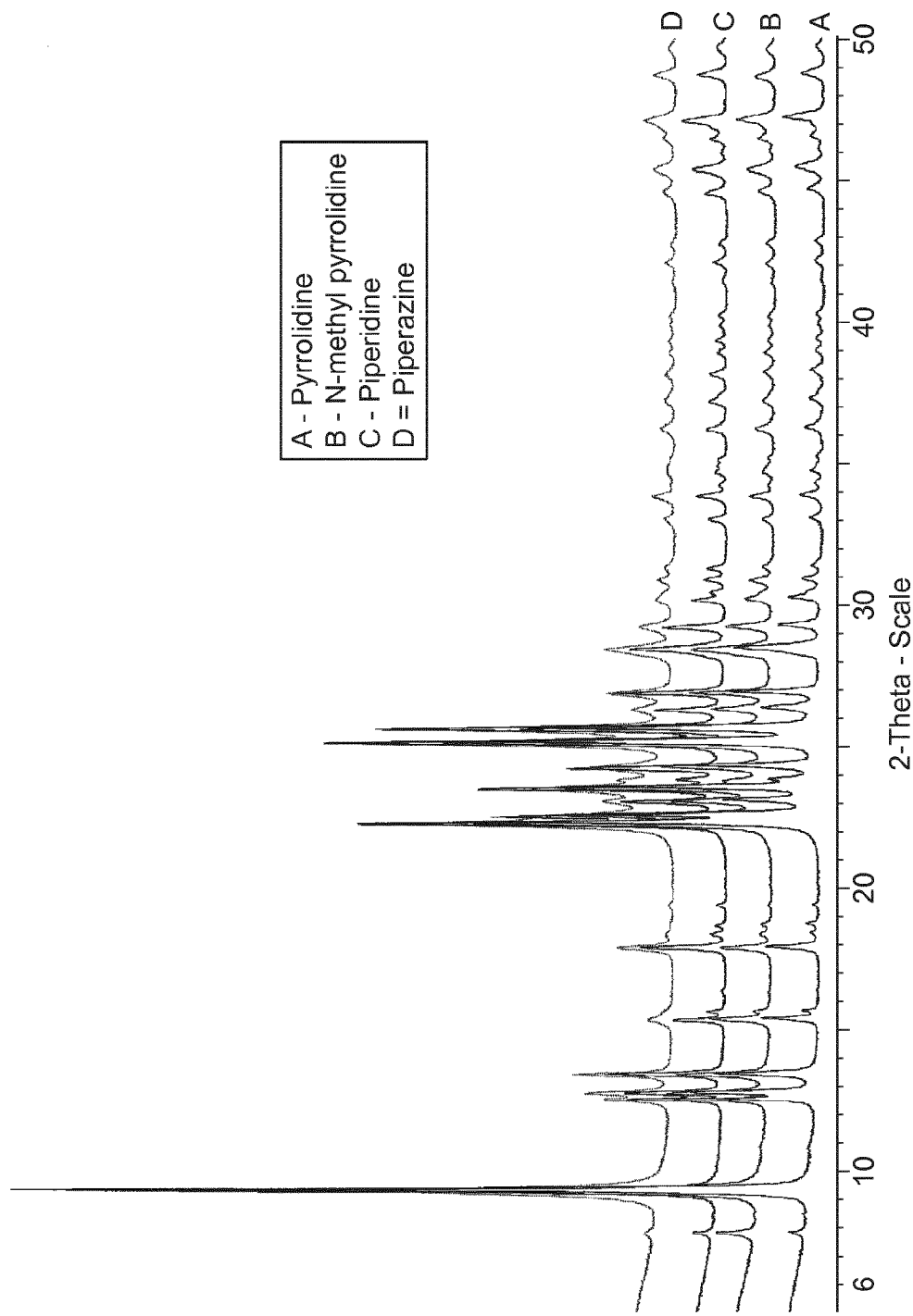
FIG. 9 provides the X-ray diffraction pattern of small crystallite ferrierites of the present invention prepared using pyrrolidine, N-methyl pyrrolidine, piperidine and piperazine.

EXAMPLE 7—ZEOLITE PREPARATION USING SATURATED NITROGEN CONTAINING HETEROCYCLIC COMPOUNDS 0.440 g of a 50% m/v solution of sodium hydroxide in de-ionised water was added to 56.58 g de-ionised water and 2.153 g sodium aluminate and mixed well using an overhead stirrer (250-300 rpm). An amount, as shown in Table 8 below, of a saturated nitrogen containing heterocyclic compound as organic structure directing agent was added to the mixture with stirring. 53.58 g Ludox AS 30 (30 wt % silica in water) was then added and stirred until a gel was formed. The gel was transferred to a stainless steel autoclave (100 mL) fitted with a Teflon liner and rotated (15 rpm) in an oven at 135° C. for 17 days. The autoclave was allowed to cool under rotation to room temperature over a period of 2 hours. The contents of the autoclave were then filtered and the solids washed with de-ionised water and dried at 90° C. overnight. A portion of the as-synthesised product was analysed by X-ray diffraction (XRD). The X-ray diffraction patterns of the as-synthesised products made using each of the various organic structure directing agents are shown in FIG. 9. In each case the XRD data demonstrated that the as-synthesised product was ferrierite.

A portion of the as-synthesised product was calcined at 550° C. for 16 hours to remove the organic structure directing agent from the pores of the zeolite. The calcined product was then converted into the ammonium form of ferrierite by ion-exchange with 1M ammonium nitrate (10 mL per gram of zeolite). The ammonium exchange was conducted at 80° C. for 1 hour and repeated three times. The ion-exchanged product was separated from the liquid by filtration, washed with deionised water and dried at 90° C. overnight. The ammonium exchanged ferrierite was converted into the hydrogen form of ferrierite by calcining in air at 500° C. for 4 hours. A portion of the hydrogen form ferrierite was pressed, crushed and sieved into particles of 100-160 microns.

The mesopore volume ($V_{mesopore}$ cm$^3$/g) for the zeolites is given in Table 9 below.

TABLE 8

| Organic structure directing agent | Mol. Wt. | Moles | Weight/g |
| --- | --- | --- | --- |
| Pyrrolidine | 71.12 | 0.166 | 11.80 |
| N-methyl pyrrolidine | 85.15 | 0.166 | 14.13 |
| Piperidine | 85.15 | 0.166 | 14.13 |
| Piperazine | 86.14 | 0.166 | 14.3 |

TABLE 9

| Organic structure directing agent | XRD Analysis | $V_{mesopore}$ (cm$^3$/g) |
| --- | --- | --- |
| Pyrrolidine | FER | 0.16 |
| N-methyl pyrrolidine | FER | 0.17 |
| Piperidine | FER | 0.11 |
| Piperazine | FER | 0.11 |

FIGS. 4 to 7 are SEM micrographs (100 K×magnification) of the products prepared using pyrrolidine, N-methyl pyrrolidine, piperidine and piperazine respectively. The products prepared using pyrrolidine, N-methyl pyrrolidine, piperidine produced ferrierite crystals of oblong morphology and the majority of the crystals had a dimension in the c-axis of about 50 to about 350 nm. At least 70% of the crystallites had a c-axis dimension in the range 50 to 250 nm and the ratio of the dimension of the c-axis to the dimension of the b-axis was <3:1. The product prepared using piperazine produced ferrierite crystals of needle-like morphology with at the majority of, at least 70%, of the crystallites having a c-axis dimension in the range 50 to 250 nm and a ratio of the dimension of the c-axis to the dimension of the b-axis of 5:1 or greater.

EXAMPLE 8—ZEOLITE PREPARATION USING POTASSIUM HYDROXIDE

Figure 10:
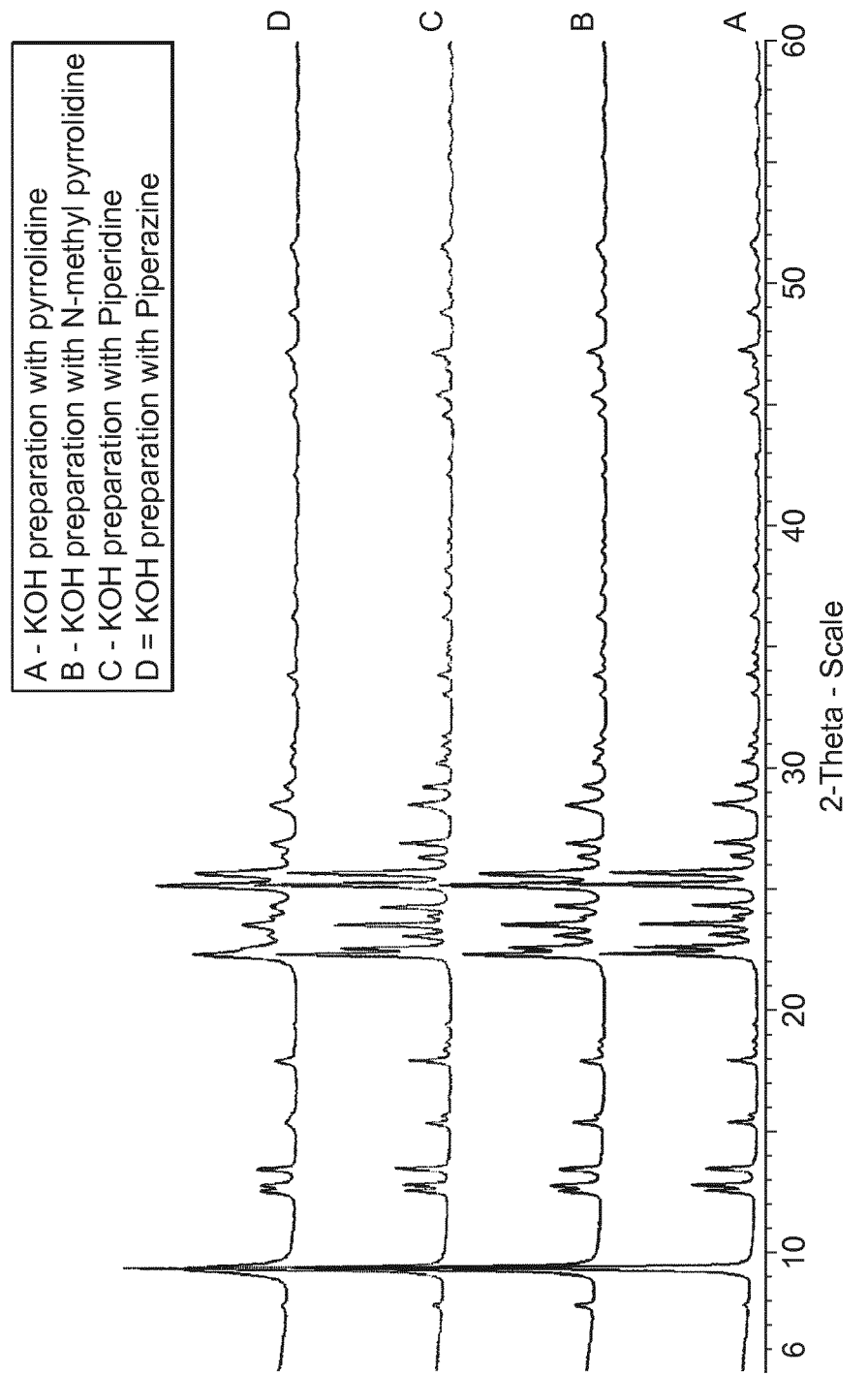
FIG. 10 provides the X-ray diffraction pattern of small crystallite ferrierites of the present invention prepared using potassium hydroxide.
Figure 11:
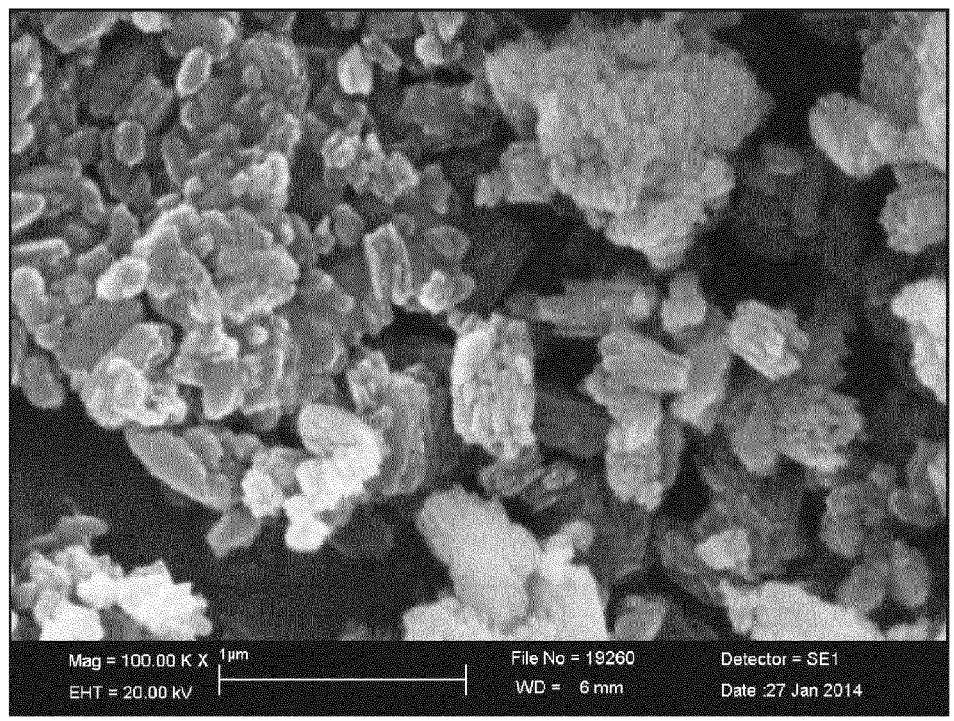
FIG. 11 is a SEM micrograph of a small crystallite ferrierite of the present invention prepared using potassium hydroxide and pyrrolidine.

Example 7 was repeated except that 0.617 g of a 50% m/v solution of potassium hydroxide in de-ionised water was used instead of the sodium hydroxide solution. The X-ray diffraction patterns of the as-synthesised products made using each of the various organic structure directing agents are shown in FIG. 10. In each case the XRD data demonstrated that the as-synthesised product was ferrierite. FIG. 11 is a SEM micrograph (100 K× magnification) of the ferrierite product prepared using pyrrolidine which shows that the majority of the ferrierite crystals (at least 70%) have a c-axis dimension in the range 50 to 250 nm and a c-axis to b-axis ratio of <3:1.

EXAMPLE C—PREPARATION USING i) UNSATURATED NITROGEN-CONTAINING HETEROCYCLIC COMPOUNDS AND ii) $C_2$-$C_4$ ALKYL AMINES

The preparation method of Example 7 was repeated using amounts of the organic structure directing agents specified in Table 10 below.

TABLE 10

| Organic structure directing agent | Mol. Wt. | Moles | Weight/g |
| --- | --- | --- | --- |
| Pyridine | 79.10 | 0.166 | 13.13 |
| Pyrrole | 67.09 | 0.166 | 11.14 |

TABLE 10-continued

| Organic structure directing agent | Mol. Wt. | Moles | Weight/g |
|---|---|---|---|
| N-methyl pyrrole | 81.12 | 0.166 | 13.46 |
| Pyrazole | 68.08 | 0.166 | 11.30 |
| Imidazole | 68.08 | 0.166 | 11.30 |
| Pyrrolidin-2-one | 85.10 | 0.166 | 14.12 |
| Ethylenediamine | 60.10 | 0.166 | 9.98 |
| Propylamine | 59.11 | 0.166 | 9.81 |
| Butylamine | 73.14 | 0.166 | 12.14 |
| Hexamethyleneimine | 99.17 | 0.166 | 16.46 |

A portion of each as-synthesised product was analysed by X-ray diffraction (XRD). The results of the XRD analysis are shown in Table 11 below.

TABLE 11

| Organic structure directing agent | XRD Analysis |
|---|---|
| Pyridine | Amorphous |
| Pyrrole | Amorphous |
| N-methyl pyrrole | Amorphous |
| Pyrazole | Amorphous |
| Imidazole | Amorphous |
| Pyrrolidin-2-one | Amorphous |
| Ethylenediamine | FER |
| Propylamine | Mixture of zeolites |
| Butylamine | Mainly ZSM-5 |
| Hexamethyleneimine | Mixture of zeolites |

The results of the XRD analysis shown in Table 11 demonstrate that the use of unsaturated heterocyclic compounds containing nitrogen and $C_3$-$C_4$ alkyl amines as organic structure directing agents do not result in the production of the small crystal ferrierite zeolites of the present invention. As may be seen from Table 11 the XRD data from the product prepared using ethylenediamine indicates that the as-synthesised product was ferrierite. The mesopore volume ($V_{mesopore}$ cm$^3$/g) for ferrierite prepared using ethylenediamine structure directing agent was found to be 0.07 cm$^3$/g.

Figure 8:
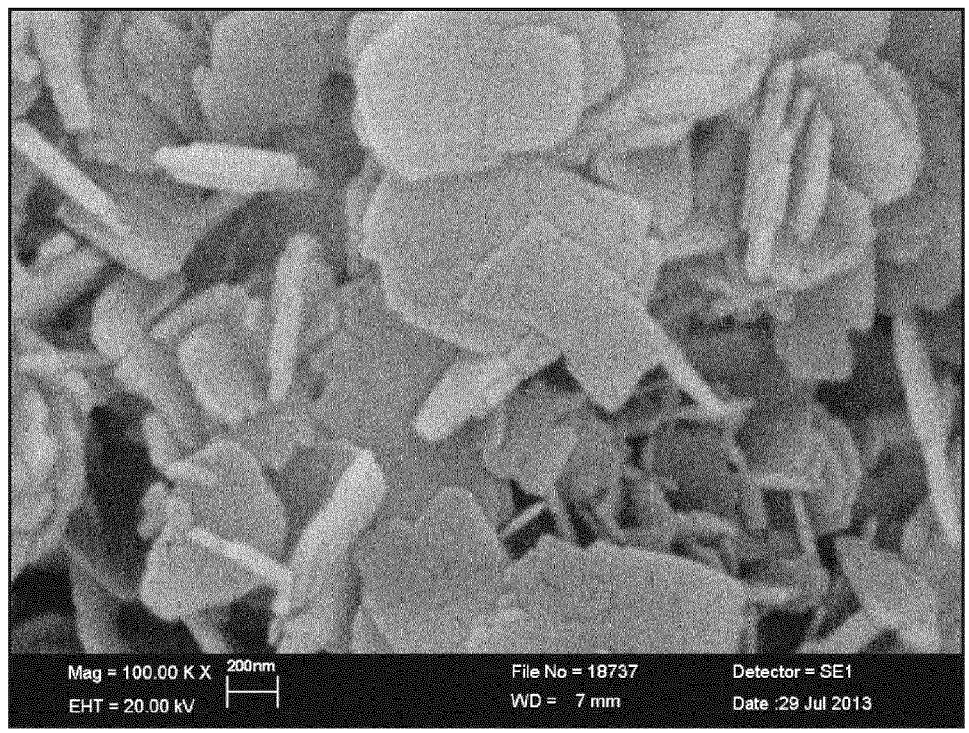
FIG. 8 is a SEM micrograph of a large crystallite ferrierite prepared using ethylenediamine structure directing agent.

FIG. 8 is a SEM micrograph (100K× magnification) of the product prepared using ethylenediamine. The SEM shows that the ferrierite crystals prepared using ethylenediamine have a platelet-like morphology with the vast majority (at least 90%) of the crystallites having a c-axis dimension of greater than 250 nm and a ratio of the dimension of the c-axis to the dimension of the b-axis of greater than 5:1.

EXAMPLE 9—DEHYDRATION-HYDROLYSIS REACTIONS

Dehydration-hydrolysis reactions of methyl acetate and methanol were carried out in the presence of i) catalysts prepared in Example 7 using pyrrolidine, N-methyl pyrrolidine and piperidine structure directing agents and ii) catalyst prepared in Example C using ethylenediamine structure directing agent. The reactions were carried out in the apparatus as described in Example 2 above using 0.015 g of the pressed, crushed and sieved catalyst particles prepared in Example 7 and Example C.

Nitrogen and helium at a total gas hourly space velocity of 16,000 h$^{-1}$ were introduced into the reactor. The pressure was increased to 30 barg and the reactor temperature adjusted to 180° C. A vapour feed of 72.0 mol % methyl acetate, 7.5 mol % methanol, 20 mol % water and 0.5 mol % acetone was introduced into the reactor at a gas hourly space velocity of 4,000 h$^{-1}$ for a period of 115 hours. The reactor temperature was then increased from 180° C. to 230° C. and held at this temperature for a period of 90 hours before reducing the temperature to 180° C. for a period of 45 hours. The reactor temperature was then increased from 180° C. to 250° C. and held at this temperature for a period of 120 hours before reducing the temperature to 180° C. for a period of 40 hours. The reactor temperature was then increased from 180° C. to 270° C. and held at this temperature for a period of 105 hours before reducing the temperature to 180° C. for a period of 45 hours.

Tables 12-14 below provides the deactivation rates of the catalysts tested in Example 10 for the reaction periods conducted at 230° C., 250° C. and 270° C. The deactivation rates were calculated as % loss in space time yield (STY) per day of each of the products dimethyl ether and acetic acid.

TABLE 12

Deactivation rates at 230° C.

| | | % STY loss/day | |
|---|---|---|---|
| Catalyst | Organic structure directing agent | Acetic Acid | Dimethyl ether |
| Ex. 7 | pyrrolidine | 1.3 | 1.0 |
| Ex. 7 | N-methyl pyrrolidine | 1.4 | 0.9 |
| Ex. 7 | piperidine | 1.3 | 0.6 |
| Ex. C | ethylenediamine | 2.4 | 2.4 |

TABLE 13

Deactivation rates at 250° C.

| | | % STY loss/day | |
|---|---|---|---|
| Catalyst | Organic structure directing agent | Acetic Acid | Dimethyl ether |
| Ex. 7 | pyrrolidine | 1.5 | 1.5 |
| Ex. 7 | N-methyl pyrrolidine | 0.7 | 0.6 |
| Ex. 7 | piperidine | 1.0 | 1.3 |
| Ex. C | ethylenediamine | 6.2 | 7.8 |

TABLE 14

Deactivation rates at 270° C.

| | | % STY loss/day | |
|---|---|---|---|
| Catalyst | Organic structure directing agent | Acetic Acid | Dimethyl ether |
| Ex. 7 | pyrrolidine | 7.3 | 8.9 |
| Ex. 7 | N-methyl pyrrolidine | 5.3 | 6.1 |
| Ex. 7 | piperidine | 6.7 | 8.1 |
| Ex. C | ethylenediamine | 12.3 | 12.6 |

As can clearly be seen from Tables 12-14 above, the FER type catalysts of the present invention (Ex. 7 catalysts) provided significantly lower deactivation rates over the temperature range 230° C. to 270° C. than the much larger crystal FER type catalyst prepared in Example C.

EXAMPLE D—EXAMPLE 1 OF U.S. Pat. No. 3,992,466

The preparation method of Example 1 of U.S. Pat. No. 3,992,466 is directed to the preparation of ZSM-35 and was repeated on a reduced scale as follows. Example 1 of the '466 patent requires sulphuric acid as a component of the acid alum solution. The concentration of the sulphuric acid used is not specified in Example 1 thus the procedure in this Example D used both 0.5 M sulphuric acid and 18M sulphuric acid. A reaction mixture was prepared from a silicate solution, an acid alum solution, pyrrolidine and water. The silicate solution was prepared from 27.08 g Ludox HS-30 (a 30 wt % solution of $SiO_2$ in water with $Na^+$ stabilising counterion) and 26.7 g water. The acid alum solution was prepared from 2.53 g $Al_2(SO_4)_3.18H_2O$, 1.69 g $H_2SO_4$ (0.5M or 18M), 5.33 g NaCl and 44.7 g $H_2O$. The silicate and acid alum solutions were mixed to form a gel and stirred vigorously at 250 rpm for one hour. 6.67 g pyrrolidine was then added to the gel. The gel was divided into two equal portions and each portion was charged into a stainless steel autoclave having a Teflon liner. The autoclaves were heated at a temperature of 105° C. (220° F.) for 72 hours with agitation by rotation. The solid products were filtered, washed with de-ionised water and dried overnight at 90° C. The dried products were analysed by XRD and the results are given in Table 15 below.

TABLE 15

| Expt. No. | $H_2SO_4$ concn. | XRD Analysis | Yield (g) |
|---|---|---|---|
| C1314004 | 0.5M | amorphous | 4.1 |
| C1314005 | 0.5M | amorphous | 4.5 |
| C1314006 | 18M | amorphous | 5.0 |
| C1314007 | 18M | amorphous | 4.3 |

The XRD pattern from each of the prepared products consisted of a slightly wavy almost flat line with no obvious peaks indicating that the products of Example 1 were amorphous in nature and that the preparation of ZSM-35 had failed.

EXAMPLE E—EXAMPLE 3 OF U.S. Pat. No. 3,992,466

The preparation method of Example 3 of U.S. Pat. No. 3,992,466 is directed to the preparation of ZSM-35 and was repeated on a reduced scale as follows. Example 3 of the '466 patent requires sulphuric acid as a component of the acid alum solution. The concentration of the sulphuric acid used is not specified in Example 3 thus the procedure in this Example E used both 0.5 M sulphuric acid and 18M sulphuric acid.

An acid alum solution prepared from 3.18 g $Al_2(SO_4)_3 \cdot 18H_2O$, 2.12 g $H_2SO_4$ (0.5M or 18M) and 19.84 g $H_2O$ was added to a silicate solution prepared from 34.14 g Ludox HS-30 (a 30 wt % solution of $SiO_2$ in water with $Na^+$ stabilising counterion) and 20.59 g water and the mixture stirred vigorously using a mechanical stirrer for 15 minutes into a thick gel. 29.76 g water was added to dilute the gel and then 4.96 g pyrrolidine was added and mixed into the gel. The gel was divided into two equal portions and each portion was charged into a stainless steel autoclave having a Teflon liner. The autoclaves were heated at a temperature of 150° C. (300° F.) for 4 days with agitation by rotation. The products were filtered, washed with de-ionised water and dried overnight at 90° C. The dried products were analysed by XRD and the results are shown in Table 16 below.

TABLE 16

| Expt. No. | $H_2SO_4$ concn. | XRD Analysis | Yield (g) |
|---|---|---|---|
| C1314041 | 0.5M | amorphous | 5.9 |
| C1314042 | 0.5M | amorphous | 5.8 |
| C1314043 | 18M | amorphous | 5.8 |
| C1314044 | 18M | amorphous | 5.4 |

The XRD pattern from each of the prepared products consisted of a slightly wavy almost flat line with no obvious peaks indicating that the products of Example 3 were amorphous in nature and that the preparation of ZSM-35 had failed.

The invention claimed is:

1. A process for the co-production of acetic acid and dimethyl ether comprising the step of contacting methyl acetate and methanol in the presence of a catalyst comprising a crystalline zeolite having a FER framework type wherein said zeolite has crystallites having a dimension of about 500 nm or less in the c-axis, the ratio of the dimension in the c-axis to the dimension in the b-axis is less than or equal to 3:1 and 1 mol % to 60 mol % of its cation-exchange capacity is occupied by cations of an alkali metal, said alkali metal being cesium.

2. The process according to claim 1 wherein the crystallites have the dimension in the c-axis of about 350 nm or less.

3. The process according to claim 2 wherein the crystallites have the dimension in the c-axis of about 250 nm or less.

4. The process according to claim 3 wherein at least 70% of the crystallites have the dimension in the c-axis of about 250 nm or less.

5. The process according to claim 1 wherein the zeolite has a mesopore volume of at least 0.1 $cm^3/g$ as measured by $N_2$ absorption.

6. The process according to claim 5 wherein the mesopore volume is 0.1 to 0.2 $cm^3/g$ as measured by $N_2$ absorption.

7. The process according to claim 1 wherein the zeolite is ferrierite.

8. The process according to claim 1 wherein the catalyst contains a refractory oxide binder.

9. The process according to claim 1 wherein water is added to the process in an amount in the range from 0.1 to 60 mol % based on the total feed to the process.

10. The process according to claim 1 wherein the process is operated in the vapour phase.

11. The process according to claim 1 wherein the process is carried out at temperatures of from 170° C. to 300° C.

12. The process according to claim 1 wherein the process is carried out at pressures in the range from atmospheric pressure to 30 barg.

13. The process according to claim 1 wherein the zeolite is prepared by forming an aqueous synthesis mixture of silica, alumina, alkali metal and a saturated nitrogen-containing heterocyclic compound and heating said mixture under stirred conditions until the aluminosilicate zeolite crystallizes.

* * * * *